(12) United States Patent
Suzuki

(10) Patent No.: US 8,221,305 B2
(45) Date of Patent: Jul. 17, 2012

(54) ENDOSCOPE TREATMENT TOOL SYSTEM

(75) Inventor: Keita Suzuki, Tokyo (JP)

(73) Assignee: Olympus Corporation (JP)

( * ) Notice: Subject to any disclaimer, the term of this patent is extended or adjusted under 35 U.S.C. 154(b) by 1125 days.

(21) Appl. No.: 12/105,872

(22) Filed: Apr. 18, 2008

(65) Prior Publication Data

US 2008/0262296 A1    Oct. 23, 2008

Related U.S. Application Data

(63) Continuation of application No. PCT/JP2005/019212, filed on Oct. 19, 2005.

(30) Foreign Application Priority Data

May 6, 2004    (JP) .................... 2004-137206

(51) Int. Cl.
*A61B 1/00* (2006.01)
*A61M 5/178* (2006.01)

(52) U.S. Cl. ............ 600/106; 600/104; 604/159

(58) Field of Classification Search ............ 600/104, 600/106, 114, 130; 475/11, 182, 300, 331, 475/339; 74/116, 405, 406, 413, 52, 567–569; 604/159

See application file for complete search history.

(56) References Cited

U.S. PATENT DOCUMENTS

| | | | | |
|---|---|---|---|---|
| 2,775,128 A | * | 12/1956 | Young | 74/49 |
| 3,721,130 A | * | 3/1973 | McKee | 74/86 |
| 3,913,409 A | * | 10/1975 | Opderbeck | 74/61 |
| 4,616,648 A | * | 10/1986 | Simpson | 606/108 |
| 5,167,589 A | * | 12/1992 | Wawrzyniak et al. | 475/169 |
| 5,540,649 A | * | 7/1996 | Bonnell et al. | 600/114 |
| 5,779,623 A | * | 7/1998 | Bonnell | 600/114 |

(Continued)

FOREIGN PATENT DOCUMENTS

GB    1 233 606    5/1971

(Continued)

OTHER PUBLICATIONS

English Translation of International Search Report and Written Opinion dated Nov. 22, 2005.

(Continued)

*Primary Examiner* — Anhtuan Nguyen
*Assistant Examiner* — Alireza Nia
(74) *Attorney, Agent, or Firm* — Ostrolenk Faber LLP

(57) ABSTRACT

An endoscope system (1) is provided with a flexible forceps insertion portion (i.e., a treatment tool insertion portion) (6) at whose distal end is provided a forceps distal end portion (i.e., a treatment tool distal end portion) (5) that receives forwards or backwards driving force and opens and closes to grip tissue, a channel (7) through which the forceps insertion portion (6) can be inserted, an insertion/extraction device (8) that inserts or extracts the forceps insertion portion (6) from within the channel (7), and an operating device (10) that supplies forwards or backwards driving force to the forceps distal end portion (5). The insertion/extraction device (8) and the operating device (10) are provided with drive shafts (13) that are driven to pivot by a motor (i.e., pivot drive source) that is fixedly supported inside an operating unit (3), rollers (15) that receive pivot driving force from the drive shafts (13) and are able to pivot so as to move the forceps insertion portion (6) forwards or backwards, and a power transmission device (16) that transmits pivot drive force from the drive shafts 13 to the rollers 15.

9 Claims, 20 Drawing Sheets

U.S. PATENT DOCUMENTS

| | | | | |
|---|---|---|---|---|
| 5,971,991 | A * | 10/1999 | Sunderland | 606/108 |
| 6,074,381 | A * | 6/2000 | Dinh et al. | 606/1 |
| 6,171,234 | B1 * | 1/2001 | White et al. | 600/102 |
| 6,358,199 | B1 * | 3/2002 | Pauker et al. | 600/114 |
| 6,726,675 | B1 * | 4/2004 | Beyar | 604/510 |
| 7,214,230 | B2 * | 5/2007 | Brock et al. | 606/139 |
| 7,387,606 | B2 * | 6/2008 | Weinberg | 600/146 |
| 7,708,685 | B2 * | 5/2010 | Okada | 600/106 |
| 7,708,687 | B2 * | 5/2010 | Bern et al. | 600/115 |
| 7,789,822 | B2 * | 9/2010 | Suzuki | 600/104 |
| 7,879,052 | B2 * | 2/2011 | Adams et al. | 606/157 |
| 7,955,252 | B2 * | 6/2011 | Suzuki et al. | 600/106 |
| 2005/0165275 | A1 * | 7/2005 | Von Felten et al. | 600/140 |
| 2006/0161043 | A1 * | 7/2006 | Neumann et al. | 600/114 |
| 2008/0032850 | A1 * | 2/2008 | Ishizuka | 475/331 |

FOREIGN PATENT DOCUMENTS

| | | |
|---|---|---|
| JP | 57-190541 | 11/1982 |
| JP | 09-000492 | 1/1997 |
| JP | 09-140663 | 6/1997 |
| JP | 09-182226 | 7/1997 |
| JP | 2003265406 | 9/2003 |
| JP | 2005218497 | 8/2005 |
| WO | WO 2007/046140 | 4/2007 |

OTHER PUBLICATIONS

European Search Reort dated May 8, 2009 in corresponding European Patent Application No. EP 05 79 5579 (English language).

Office Action (Notice of Allowance) dated Jan. 5, 2010 issued in connection with counterpart Japanese Application No. 2004-137206 (and English language translation).

* cited by examiner

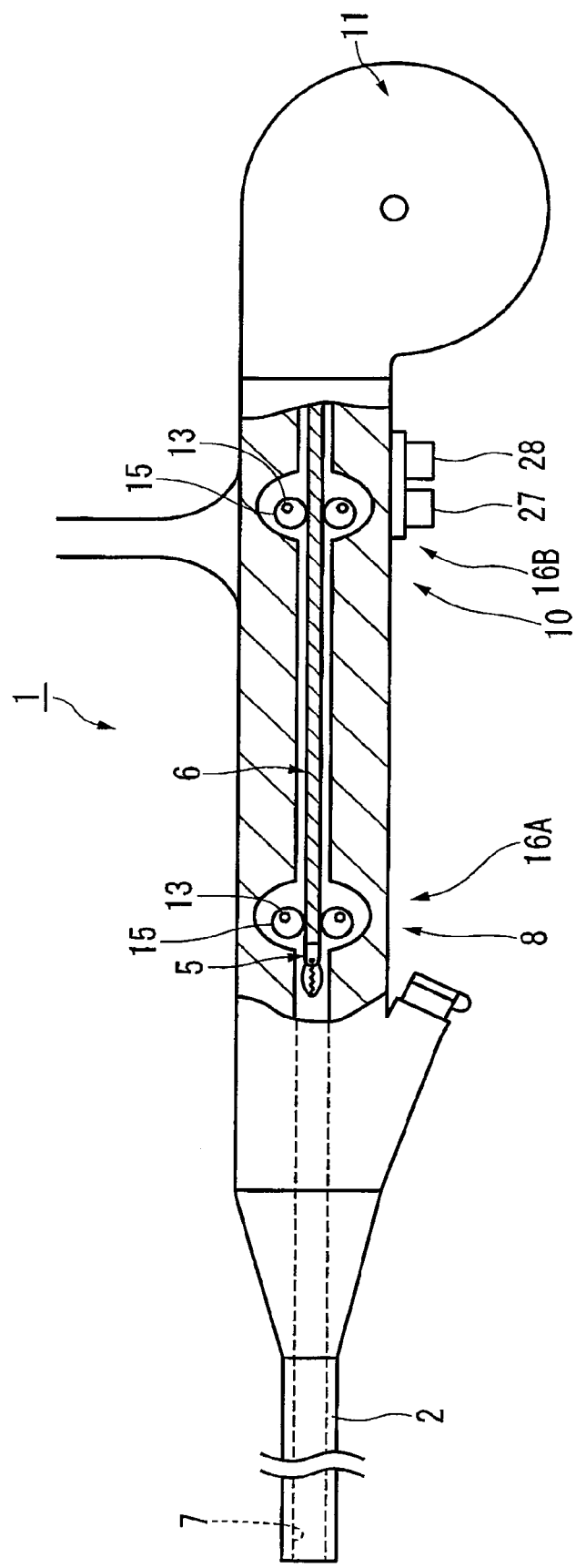

ENDOSCOPE TREATMENT TOOL SYSTEM

TECHNICAL FIELD

The present invention relates to an endoscope system. This application is a continuation application based on a PCT Patent Application No. PCT/JP2005/019212, filed Oct. 19, 2005. The contents of the PCT Application are incorporated herein by reference.

BACKGROUND ART

Generally, when a portion inside a body requires treatment or when biological tissue inside a body is to be examined by means of operations performed outside the body using an endoscope, there are cases when a plurality of treatment tools such as, for example, needle scalpels and gripping forceps are used consecutively. In such cases, conventionally, operations are performed such as inserting a selected treatment tool into the body through a channel that is provided inside an insertion portion of the endoscope, and then extracting the treatment tool to the outside of the body after predetermined treatment has been performed, and then once more inserting another treatment tool into the channel.

When inserting a treatment tool into the channel, it is currently necessary to insert the elongated treatment tool extremely carefully into the narrow channel through a forceps channel provided in the endoscope, so that not only is the task laborious, but it also requires a high level of concentration. Moreover, in recent years, treatment tool insertion portions having various outer diameters, and treatment tools in which the treatment tool distal end portions and the treatment tool insertion portions have different outer diameters have been proposed to suit the type of operation or to match the outer diameter of the channel of an endoscope.

Because of this, in order to provide insertion/extraction devices that perform these operations to insert or extract a treatment tool into a channel automatically, and that are able to handle treatment tools having different diameters, devices have been proposed in which there is provided separately from the insertion/extraction roller a rotary solenoid that switches between a state in which the roller and the treatment tools having different diameters are in contact and a state in which they are mutually isolated (see, for example, Patent document 1), and also devices have been proposed in which rollers having different diameters can be replaceably mounted in accordance with the outer diameter of the treatment tool insertion portion which is being used (see, for example, Patent document 2).

[Patent document 1] Japanese Patent Application, First Publication No. Sho57-190541
[Patent document 2] Japanese Patent Application, First Publication No. Hei9-492

DISCLOSURE OF THE INVENTION

The present invention employs the following devices.

The present invention is an endoscope system that includes: a flexible treatment tool insertion portion; a channel through which the treatment tool insertion portion can be inserted; and an insertion extraction device that inserts the treatment tool insertion portion into the channel and extracts the treatment tool insertion portion from within the channel, wherein the insertion/extraction device is provided with: drive shafts that are driven by a pivot drive source to pivot; rollers that have rotation center shafts, and that receive pivot driving force from the drive shafts, and are thereby able to pivot around the rotation center shafts so as to move the treatment tool insertion portion forwards or backwards; and power transmitting devices that transmit pivot driving force from the drive shafts to the rollers, and wherein the pivot center shafts can be made to revolve around the drive shafts by rotation driving force from the drive shafts, and if a distance between the pivot center shafts and the drive shafts is set as a revolution radius, then a first distance which is obtained by adding a radius of the rollers to the revolution radius is a longer distance than a second distance between the drive shafts and the treatment tool insertion portion, and the power transmitting devices cause the pivot center shafts to revolve around the drive shafts, and cause the rollers to rotate around the pivot center shafts.

In the present invention, it is also possible for there to be provided a treatment tool distal end portion that is positioned at a distal end of the treatment tool insertion portion, and performs treatment after receiving forwards or backwards driving force, and an operating device that supplies the forwards or backwards driving force to the treatment tool distal end portion, and for the operating device to be provided with the drive shafts, the rollers, and the power transmission devices.

In the present invention, it is also possible for the power transmission devices to be formed as planetary gear mechanisms that are provided with a plurality of planetary gears and a sun gear, and for the drive shafts to be connected to one of the plurality of planetary gears, and for the rollers to be formed as internal gears that mesh with the planetary gears which are provided such that they are able to pivot around the sun gear.

In the present invention, it is also possible for the power transmission devices to be provided with a supporting component that has one end that is slidably connected to the drive shaft and has another end that is supported such that it is able to pivot around the pivot center shaft of the roller, a first pulley that is connected to the drive shaft, a second pulley that is connected to the roller, and an endless belt that is wound around the first pulley and the second pulley.

In the present invention, it is also possible for the power transmission devices to be provided with a supporting component that has one end that is slidably connected to the drive shaft and has another end that is pivotably connected to the pivot center shaft of the roller, a first gear that is connected to the drive shaft, a second gear that is connected to the roller, and a third gear that is provided such that it is able to pivot for the supporting component and meshes with the first gear and the second gear.

In the present invention, it is also possible for the power transmission device to be provided with a first gear that is connected to the drive shaft, and a supporting roller that faces the roller via the treatment tool insertion portion and meshes with the first gear.

In the present invention, it is also possible for a gripping portion that is able to rotate the drive shaft to be connected.

In the present invention, it is also possible for the treatment tool insertion portion to be provided with an outer cannula that is formed by winding at least one wire in a coil shape, and for recessed portions that are capable of meshing with the wire and protruding portions that are capable of meshing with gaps between adjacent wires to be formed alternatingly in a circumferential direction on an outer circumferential surface of the roller.

In the present invention, it is also possible for a plurality of the aforementioned wires to be provided, and for at least one of the wires to be formed having a larger diameter than the other wires.

In the present invention, it is also possible for a wire component to be wound in a coil shape onto an outer circumference of the outer cannula.

Generally, the present invention comprises an endoscope system comprising:

a flexible treatment tool insertion portion;

a channel through which the treatment tool insertion portion can be inserted; and an insertion/extraction device configured to insert the treatment tool insertion portion into the channel and extract the treatment tool insertion portion from within the channel.

A treatment tool distal end portion is positioned at a distal end of the treatment tool insertion portion, and configured to perform treatment after receiving forwards or backwards driving force. The endoscope system further comprises an operating device configured to supply the forwards or backwards driving force to the treatment tool distal end portion, wherein the insertion/extraction and the operating device are provided with: drive shafts that are driven by a pivot drive source to pivot; rollers that have rotation center shafts, and that are configured receive pivot driving force from the drive shafts, and are thereby able to pivot around the rotation center shafts.

The insertion/extraction and the operating device further comprise a first power transmitting device that is positioned at a distal end side of the channel, and configured to transmit pivot driving force from the drive shafts to the rollers, and a second power transmitting device that is positioned at a proximal end side of the channel, and configured to transmit pivot driving force from the drive shafts to the rollers.

A position of the rotation center shafts is such that, in case of the rollers contact with the treatment tool insertion portion, it is different from a position of the rotation center shafts, in case of the rollers not being in contact with the treatment tool insertion portion.

The rotation center shafts are configured such that they can be made to revolve around the drive shafts by rotation driving force from the drive shafts, with a revolution radius being defined by a distance between the rotation center shafts and the drive shafts. A first distance, which is obtained by adding a radius of the rollers to the revolution radius, is a longer distance than a second distance between the drive shafts and the treatment tool insertion portion. The first and second power transmitting devices are configured to cause the rotation center shafts to revolve around the drive shafts and to cause the rollers to rotate around the pivot center shafts. The insertion/extraction device is configured to operate the first and second power transmitting devices so as to move the treatment tool insertion portion forwards or backwards, and the operating device is configured to operate the second power transmitting device so as to perform treatment with the treatment tool distal end portion.

BRIEF DESCRIPTION OF THE DRAWINGS

FIG. 7 is an explanatory view showing an operating method of the endoscope system according to the first embodiment of the present invention.

BEST MODE FOR CARRYING OUT THE INVENTION

A first embodiment of the present invention will now be described with reference made to FIGS. 1 through 7.

Figure 1:
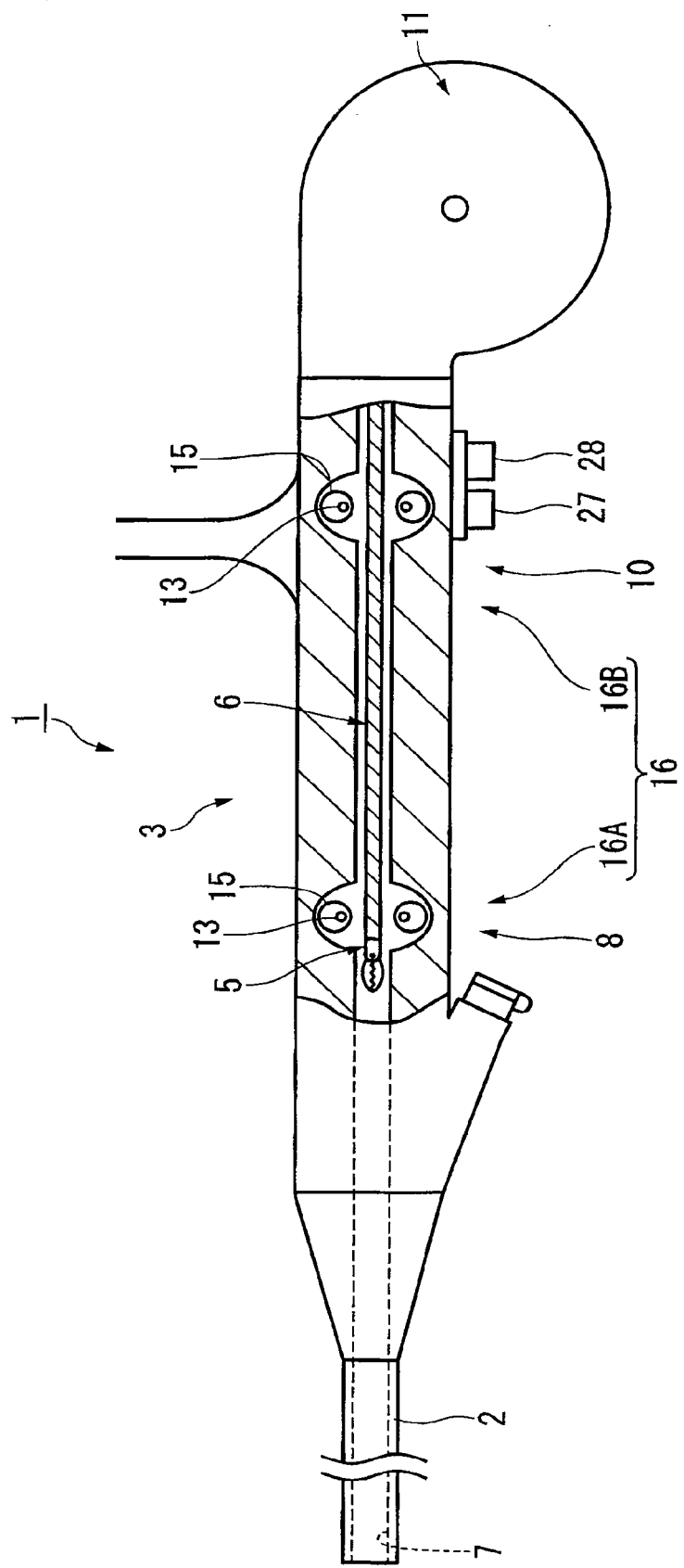
FIG. 1 is a side view including a partial cross-section which shows an endoscope system according to a first embodiment of the present invention.

As is shown in FIG. 1, an endoscope system 1 according to the present embodiment is provided with a flexible insertion portion 2, an operating unit 3 that operates the insertion portion 2, a flexible forceps insertion portion (i.e., a treatment tool insertion portion) 6 at whose distal end is provided a forceps distal end portion (i.e., a treatment tool distal end portion) 5 that receives forwards or backwards driving force and opens and closes to grip tissue, a channel 7 through which the forceps insertion portion 6 can be inserted, an insertion/extraction device 8 that inserts and extracts the forceps insertion portion 6 from within the channel 7, an operating device 10 that supplies forwards or backwards driving force to the forceps distal end portion 5, and a housing portion 11 that is connected to the operating unit 3 and houses the forceps insertion portion 6.

Figure 2:
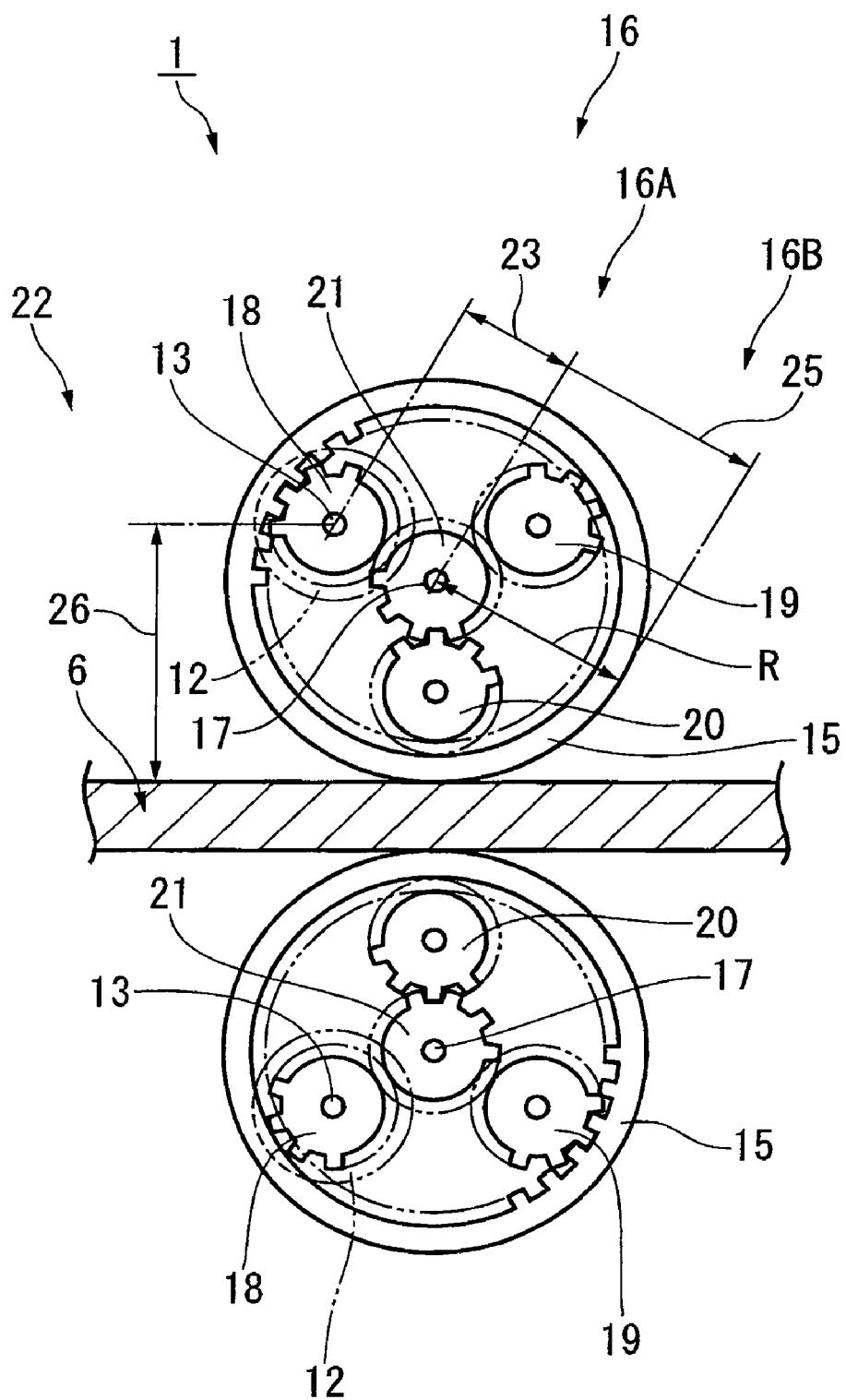
FIG. 2 is a cross-sectional view showing principal portions of a power transmission device of the endoscope system according to the first embodiment of the present invention.

As is shown in FIG. 2, the insertion/withdrawal device 8 and the operating device 10 are provided with driveshafts 13 that are driven to pivot by motors (i.e., pivot drive sources) 12 that have an attached brake and are fixedly supported inside the operating unit 3, rollers 15 that receive pivot drive force from the driveshafts 13 and are able to pivot so as to move the forceps insertion portion 6 forwards or backwards, and a power transmission device 16 that transmits pivot drive force from the driveshafts 13 to the rollers 15.

Outer circumferential surfaces of the rollers 15 which are in contact with the forceps insertion portion 6 have a concave shape, and are formed such that the surface area which is in contact with the forceps insertion portion 6 is enlarged.

The power transmission device 16 is in the form of a planetary gear mechanism 22 that is provided, for example, with three planetary gears 18, 19, and 20 and a sun gear 21 that cause the pivot center shafts 17 of the rollers 15 to revolve around the drive shafts 13, and cause the rollers 15 to rotate around the pivot center shafts 17. The drive shafts 13 are connected to the planetary gears 18 so as to form fixed gears, and the rollers 15 are formed as internal gears that engage with the planetary gears 18, 19, and 20 that are provided so as to be able to pivot around the sun gear 21. This power transmission device 16 is provided with a first power transmission device 16A that is positioned on the distal end side of the operating unit 3, and a second power transmitting device 16B that is positioned further away from the distal end of the channel 7 than the length of the protrusion of the forceps distal end portion 5 on the base end side of the first power transmitting device 16A. The first power transmission device 16A and the second power transmission device 16B together form a pair of planetary gear mechanisms 22 that face each other via the forceps insertion portion 6.

The size of each gear is adjusted such that, if the distance between the pivot center shafts 17 and the drive shafts 13 is set as a revolution radius 23, a first distance 25 which is obtained by adding a radius R of the roller 15 to the revolution radius 23 is a longer distance than a second distance 26 between the drive shafts 13 and the forceps insertion portion 6.

An insertion/extraction switch 27 that issues a command to the insertion/extraction device 8 to perform an operation to insert or extract the forceps insertion portion 6, and an operating switch 28 that issues a command to the operating device 10 to operate the forceps distal end portion 5 are placed on the operating unit 3.

The motor 12, the insertion/extraction switch 27, and the operating switch 28 are connected to a power supply unit and a control unit (not shown).

Figure 5:
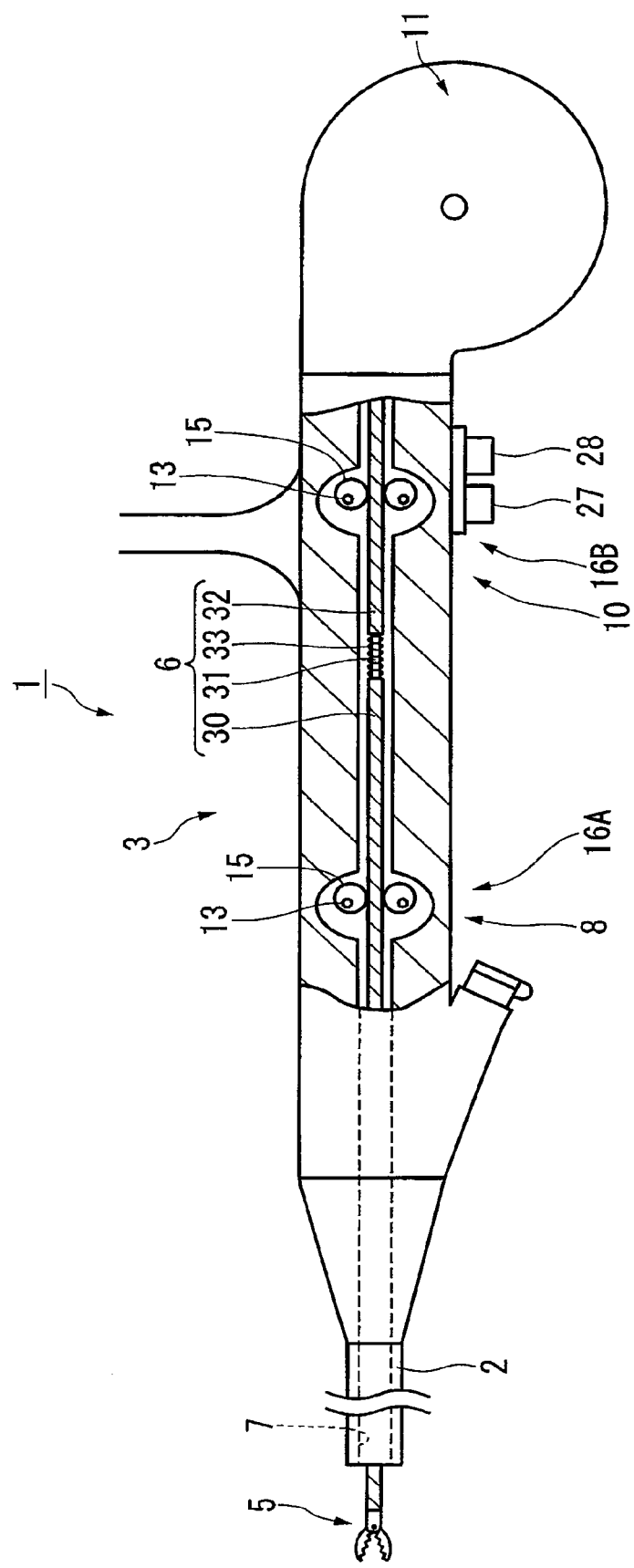
FIG. 5 is an explanatory view showing an operating method of the endoscope system according to the first embodiment of the present invention.

As is shown in FIG. 5, the forceps insertion portion 6 is provided with an outer cannula 30 whose distal end is connected to the forceps distal end portion 5, an operating wire 31 that can be moved freely forwards or backwards relative to the outer cannula 30 and that transmits forwards or backwards driving force to the forceps distal end portion 5, an operating tube 32 that is positioned on a base end side a predetermined distance away from the outer cannula 30 and that is connected to the base end side of the operating wire 31, and a spring 33 that is positioned between the outer cannula 30 and the operating tube 32 and that provides urging force to prevent the outer cannula 30 and the operating tube 32 from touching each other when the forceps insertion portion 6 is moving inside the channel 7.

Next, an operating method as well as actions and effects of the endoscope system 1 according to the present embodiment will be described.

Firstly, in the state shown in FIG. 1, the insertion portion 2 is inserted into a body cavity and the distal end of the insertion portion 2 is moved to a desired position.

Next, in order to move the forceps insertion portion 6 in the direction of the distal end of the channel 7, the insertion/extraction switch 27 is operated which drives the respective motors 12 in the first power transmitting device 16A and the second power transmitting device 16B to rotate in the same direction and at the same speed.

At this time, in conjunction with the rotation of the planetary gears 18 to which the drive shafts 13 are connected, the other planetary gears 20, the sun gears 21, and the rollers 15 are rotated respectively so as to revolve around the planetary gears 18.

Figure 3:
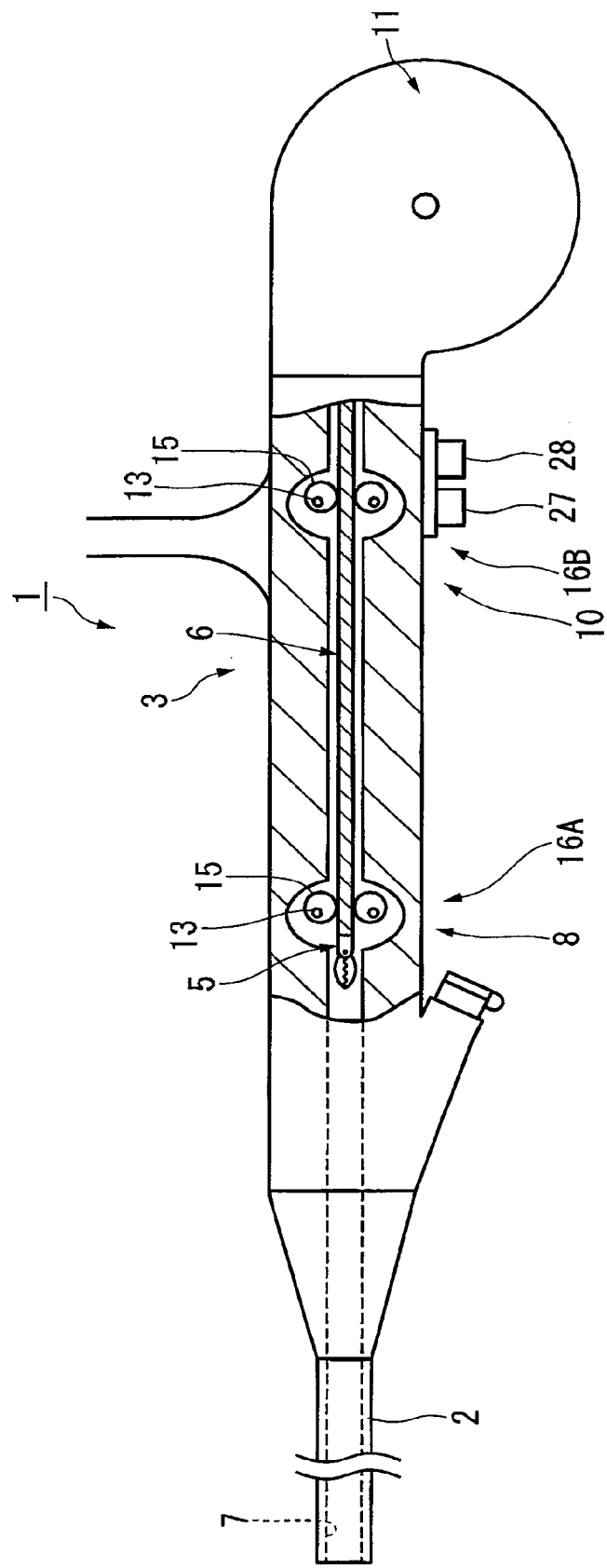
FIG. 3 is an explanatory view showing an operating method of the endoscope system according to the first embodiment of the present invention.
Figure 4:
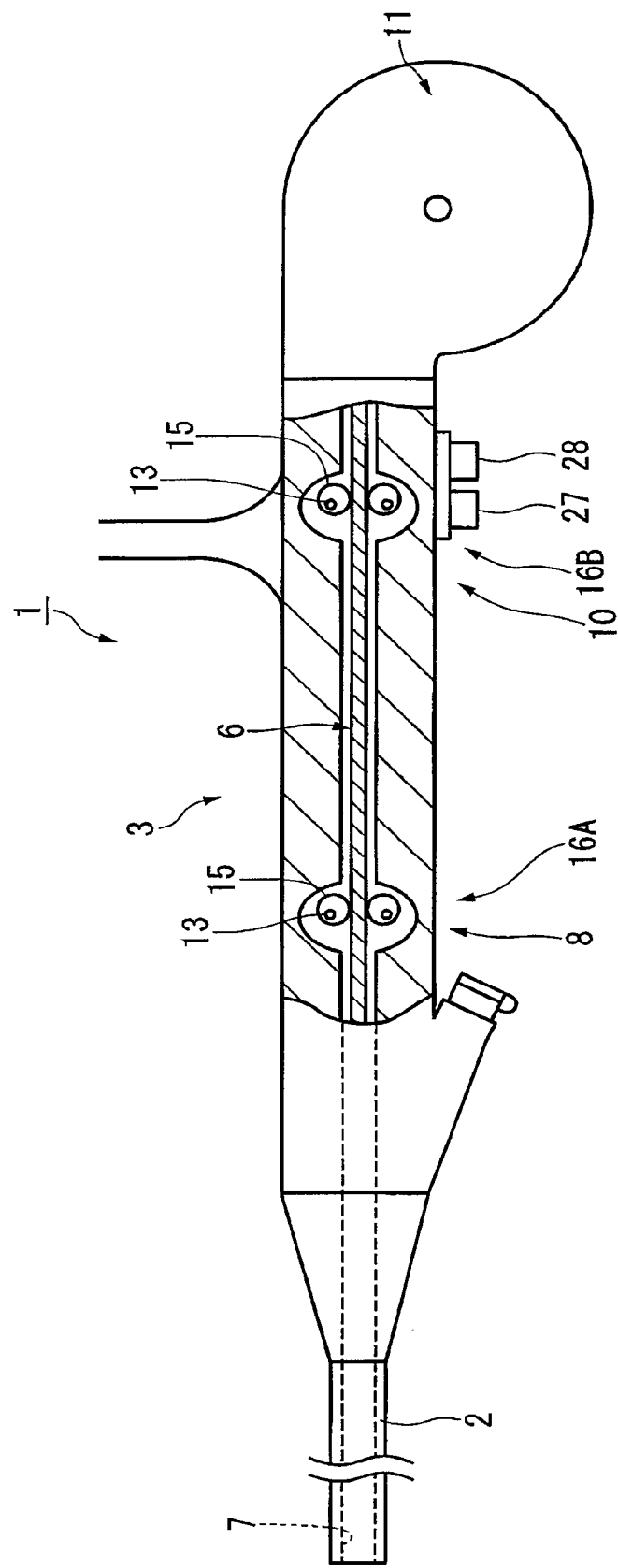
FIG. 4 is an explanatory view showing an operating method of the endoscope system according to the first embodiment of the present invention.

Next, while being rotated in the rotation direction of the planetary gears 18, the rollers 15 approach the forceps insertion portion 6 until, as is shown in FIG. 3, the rollers 15 come up against the forceps insertion portion 6. In this position, the rollers 15 continue to rotate so that the forceps insertion portion 6 which is being pressed between the rollers 15 is moved along the channel 7 as is shown in FIG. 4.

After the forceps distal end portion 5 has been made to protrude from the distal end of the channel 7, the insertion/extraction switch 27 is operated so that the motors 12 are temporarily halted.

Next, the operating switch 28 is operated so that only the motor 12 that drives the second power transmission device 16B is rotated in the same direction as that is described above. At this time, because the planetary gears 18 of the first power transmission device 16A have been stopped, the outer cannula 30 remains gripped by the rollers 15 of the first power transmission device 16A. In contrast, in conjunction with the rotation of the rollers 15 of the second power transmission device 16B, the operating tube 32 is moved further in the direction of the distal end of the channel 7.

Accordingly, the operating wire 31 moves together with the operating tube 32 so that forwards or backwards driving force is transmitted to the forceps distal end portion 5 and, as is shown in FIG. 5, the forceps distal end portion 5 is opened by means of a link mechanism (not shown).

In order for the forceps distal end portion 5 to grip tissue and then close, the operating switch 28 is operated so that the motor 12 of the second power transmission device 16B is rotated in a different direction from that described above.

Figure 6:
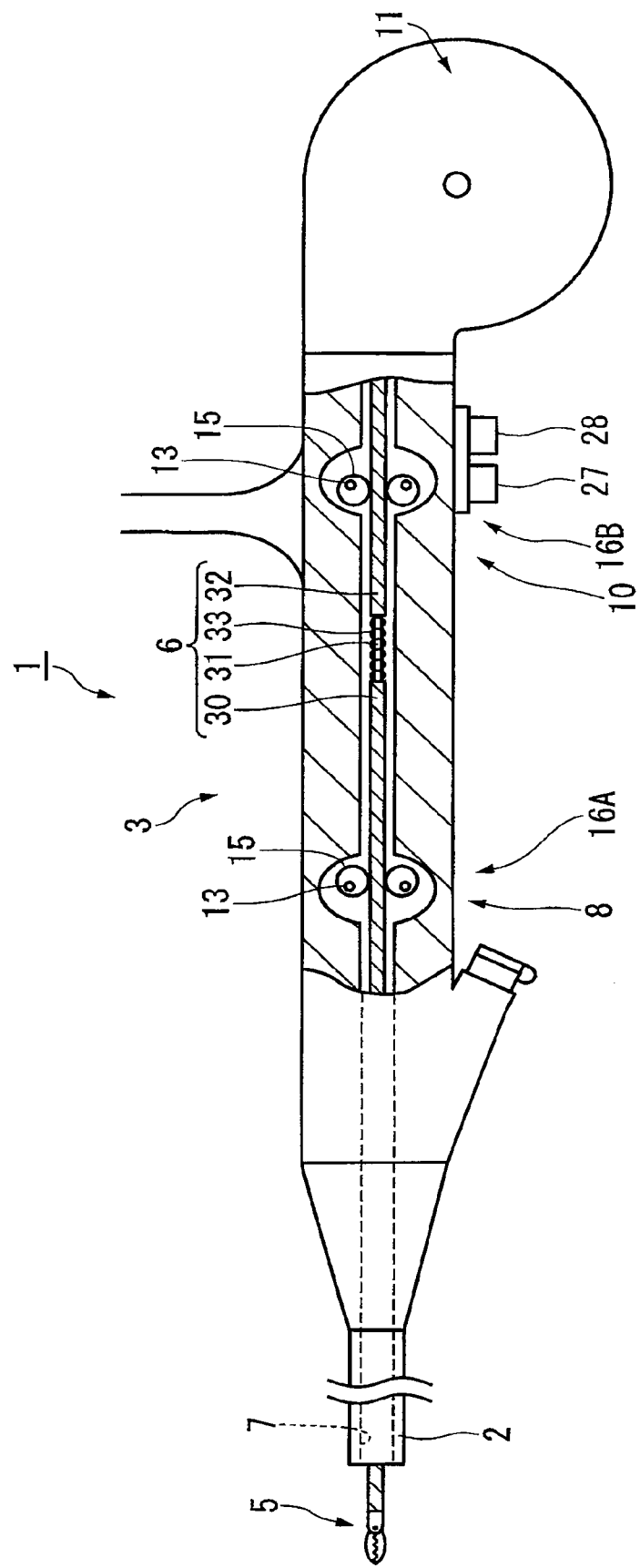
FIG. 6 is an explanatory view showing an operating method of the endoscope system according to the first embodiment of the present invention.

At this time, as the planetary gears 18 rotate, the rollers 15 move away temporarily from the operating tube 32 while rotating in the same direction as the planetary gears 18 and revolve in this direction around the planetary gears 18. As a result, they once again come into contact with the operating tube 32. After this contact, the rollers 15 rotate while being pressed against the operating tube 32 so that, as is shown in FIG. 6, the operating tube 32 and the operating wire 31 move to the base end side of the channel 7, and the forceps distal end portion 5 is closed by means of a link mechanism (not shown).

Next, the insertion/extraction switch 27 is operated thereby driving the respective motors 12 of the first power transmission device 16A and the second power transmission device 16B. At this time, the rollers 15 of the first power transmission device 16A move away temporarily from the outer cannula 30 around the planetary gears 18 while rotating in the same direction as the planetary gears 18 and revolve in this direction. As a result, they once again come into contact with the outer cannula 30. After this contact, the respective rollers 15 rotate while being pressed against the forceps insertion portion 6 so that, as is shown in FIG. 7, the forceps insertion portion 6 is moved to the base end side of the channel 7.

According to this endoscope system 1, if the drive shafts 13 are rotated in a direction so as to cause the forceps insertion portion 6, which has been inserted into the channel 7, to move forwards or backwards inside the channel 7, then it is possible to cause the rollers 15 to revolve around the drive shafts 13 while the sun gears 21 and the rollers 15 (which are internal gears) are rotated respectively around the planetary gears 18 by the power transmission device 16, and the rollers 15 can thus be placed in contact with the forceps insertion portion 6. At this time, even if forceps insertion portions 6 having different outer diameters are used, because the rollers 15 can be rotated in the same direction as the drive shafts 13 around their pivot center shafts 17 while pressing against the forceps insertion portion 6 at positions where the rollers 15 are in contact with the forceps insertion portion 6, the rollers 15 can be placed in contact with the forceps insertion portion 6 and cause it to move irrespective of the size of the outer diameter of the forceps insertion portion 6 that is being inserted into or extracted from the channel 7.

Accordingly, it is possible to deal with forceps insertion portions 6 having different outer diameters using only the motors 12 for rotating the rollers 15.

Next, a second embodiment of the present invention will be described with reference made to FIGS. 8A through 14.

Note that component elements that are the same as those in the above described first embodiment are given the same descriptive symbols and a description thereof is omitted.

Figure 8A:
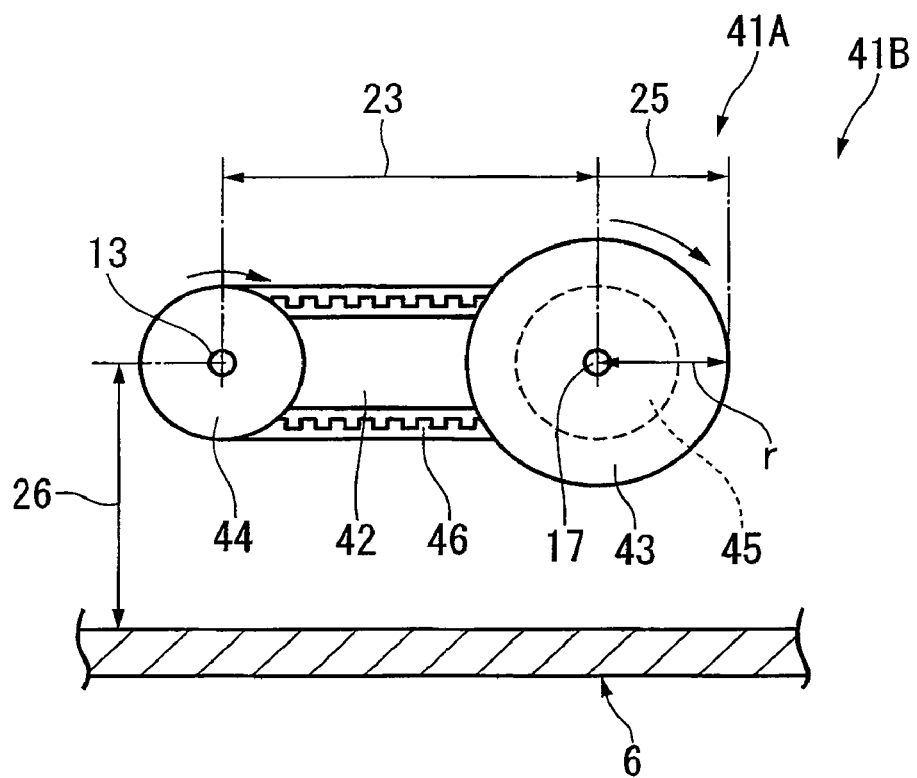
FIG. 8A is a plan view showing principal portions of a power transmission device of an endoscope system according to a second embodiment of the present invention.
Figure 8B:
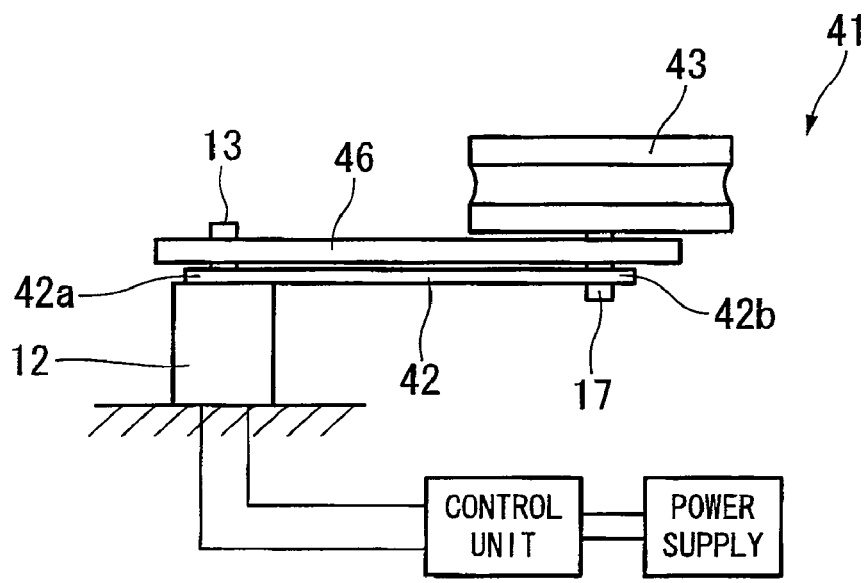
FIG. 8B is a side view showing principal portions of the power transmission device of the endoscope system according to the second embodiment of the present invention.

The second embodiment differs from the first embodiment in that, as is shown in FIGS. 8A and 8B, a power transmission device 41 of an endoscope system 40 of the present embodiment is provided with a supporting component 42 having one end 42a that is slidably connected to a drive shaft 13 and another end 42b that pivotably supports a pivot center shaft 17 of a roller 43, a first pulley 44 that is connected to the drive shaft 13, a second pulley 45 that is connected to the roller 43, and an endless belt 46 that is wound around the first pulley 44 and the second pulley 45.

Frictional force between the one end 42a of the supporting component 42 and the drive shaft 13 is set so as to be larger than the frictional force between the other end 42b and the pivot center shaft 17, and is set large enough that, when movement of the supporting component 42 is restricted, it is able to rotate relative to the drive shaft 13.

When the distance between the pivot center shaft 17 and the drive shaft 13 is set as the revolution radius 23, then a first distance 25 which is obtained by adding a radius r of the roller 43 to the revolution radius 23 is adjusted so as to be a longer distance than a second distance 26 between the drive shafts 13 and the forceps insertion portion 6.

Next, an operating method as well as actions and effects of the endoscope system 40 according to the present embodiment will be described.

Figure 9:
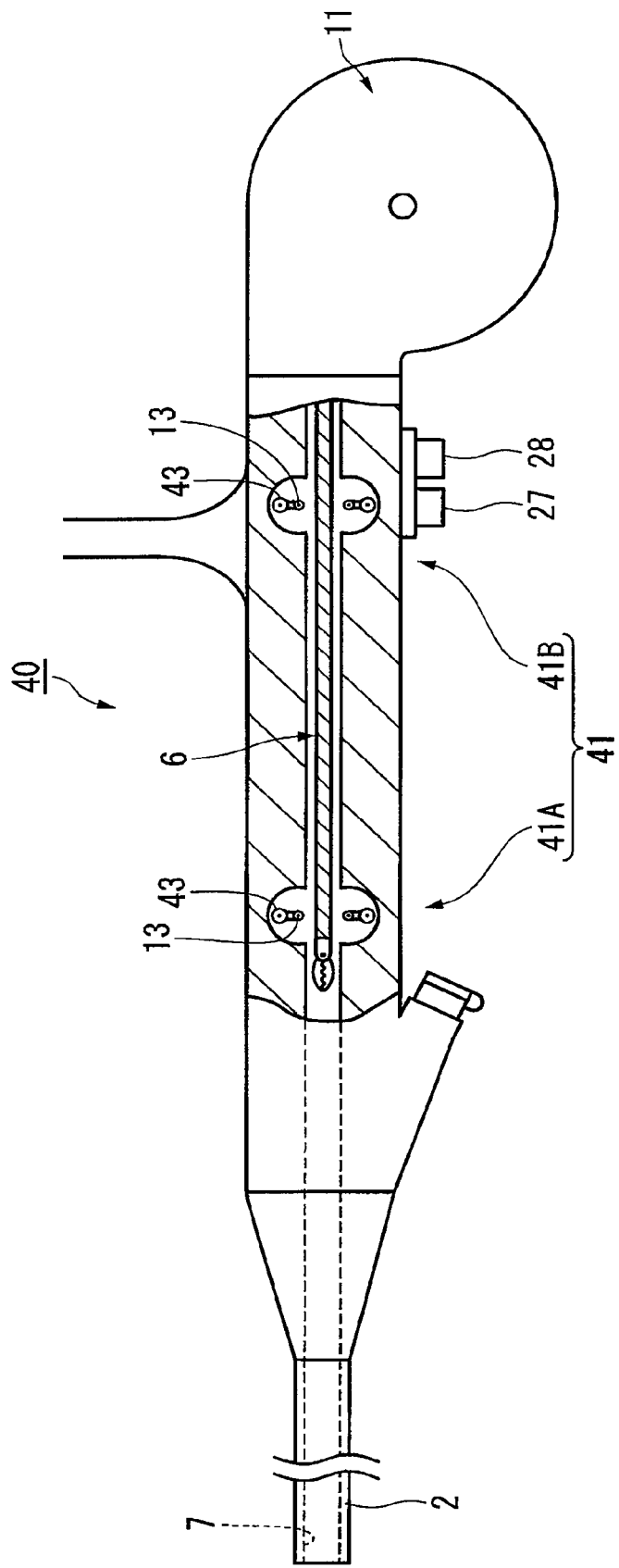
FIG. 9 is an explanatory view showing an operating method of the endoscope system according to the second embodiment of the present invention.

Firstly, in the present embodiment as well, in the state shown in FIG. 9, the insertion portion 2 is inserted into a body cavity.

Next, the insertion/extraction switch 27 is operated which drives the respective motors 12 in the first power transmitting device 16A and the second power transmitting device 16B to rotate in the same direction and at the same speed.

At this time, in conjunction with a rotation of the first pulleys 44 to which the drive shafts 13 are connected, the supporting components 42 rotate with the one end 42a as the center of rotation, while the rollers 43 revolve in the rotation direction of the first pulley 44 around the first pulley 44 together with the second pulley 45 to which the other end 42b is connected.

Figure 10:
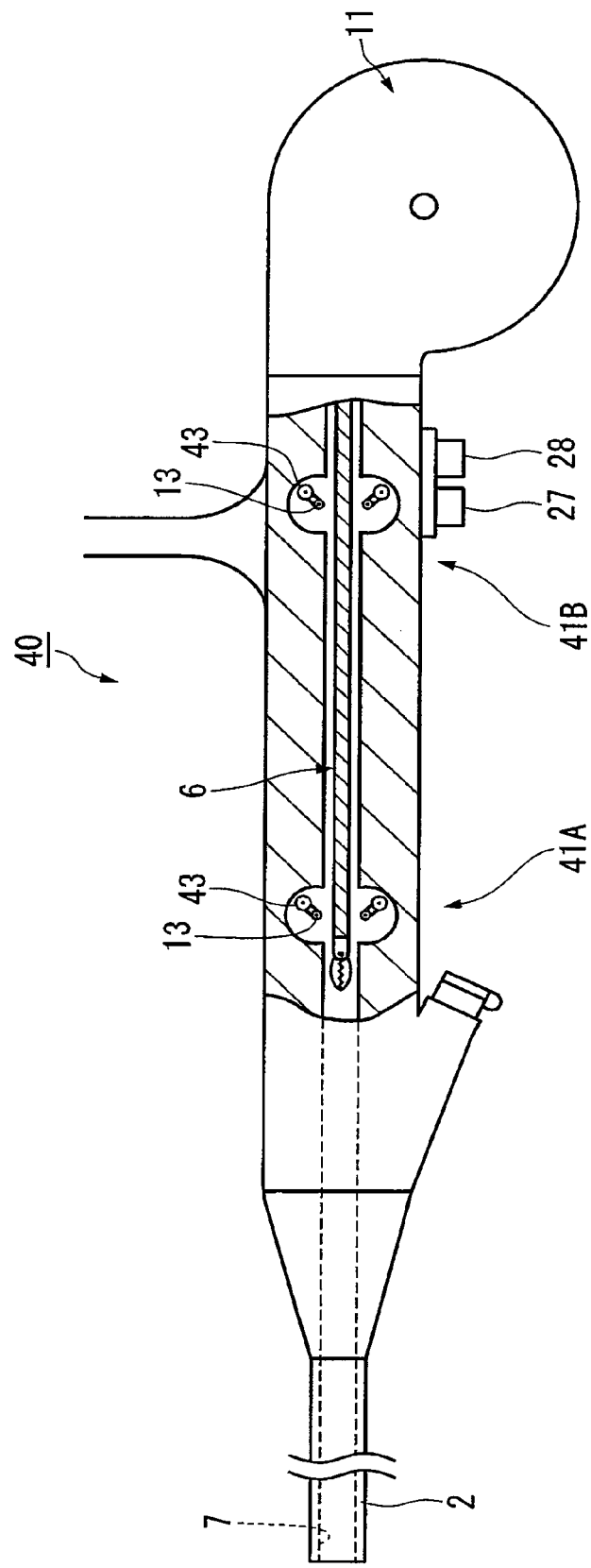
FIG. 10 is an explanatory view showing an operating method of the endoscope system according to the second embodiment of the present invention.
Figure 11:
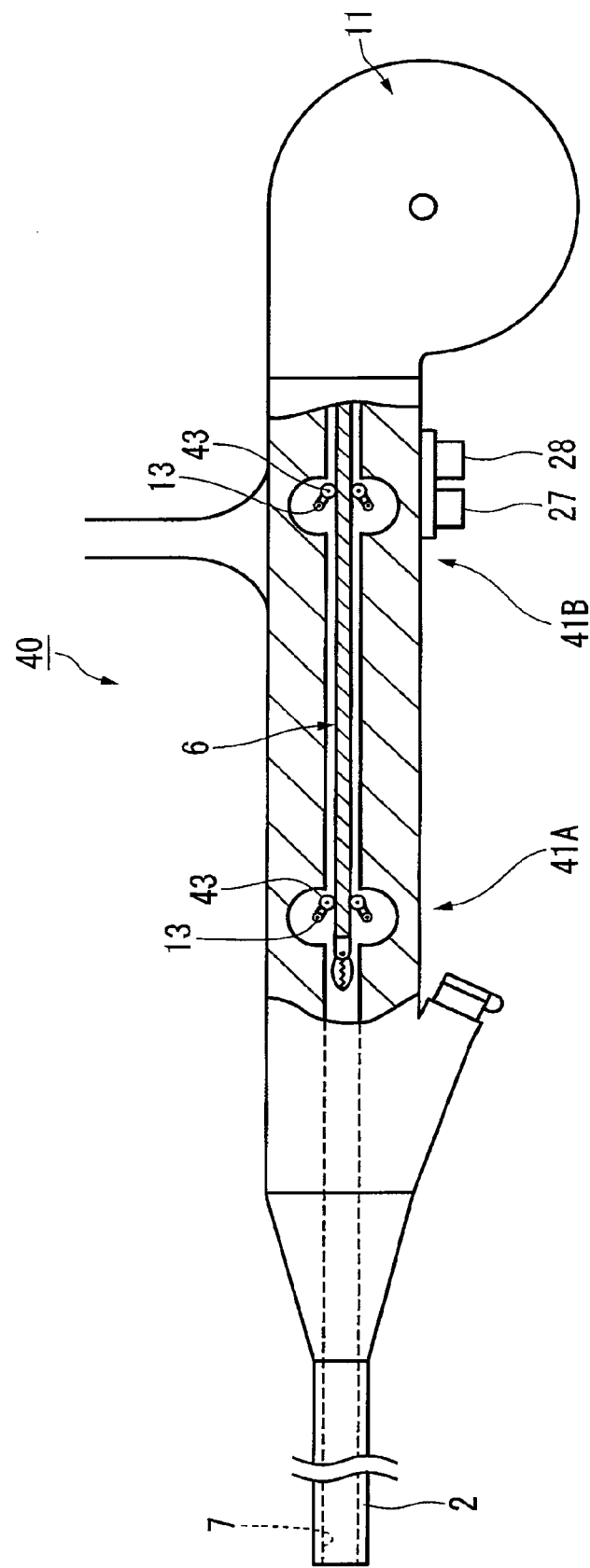
FIG. 11 is an explanatory view showing an operating method of the endoscope system according to the second embodiment of the present invention.

In addition, as is shown in FIG. 10, the rollers 43 move in the rotation direction of the first pulleys 44 so as to approach the forceps insertion portion 6 and, as is shown in FIG. 11, the rollers 43 come into contact with the forceps insertion portion 6. At this time, as the supporting components 42 are stopped, the drive shafts 13 and the supporting component 42 are idling freely, and the rotation force of the first pulley 44 is transmitted via the endless belt 46 to the second pulley 45 so that the rollers 43 continue to rotate in the same direction as the drive shaft 13. As a result, the forceps insertion portion 6 which is being pressed between the rollers 43 moves through the channel 7.

After the forceps distal end portion 5 has been made to protrude from the distal end of the channel 7, the insertion/extraction switch 27 is operated so that the motors 12 are temporarily halted.

Next, the operating switch 28 is operated so that only the motor 12 that drives the second power transmission device 16B is rotated in the same direction as that is described above. At this time, because the motor 12 of the first power transmitting device 16A remains stopped, the outer cannula 30 remains gripped by the rollers 43 of the first power transmission device 16A. In contrast, in conjunction with the rotation of the rollers 43 of the second power transmission device 16B, the operating tube 32 is moved further in the direction of the distal end of the channel 7.

Figure 12:
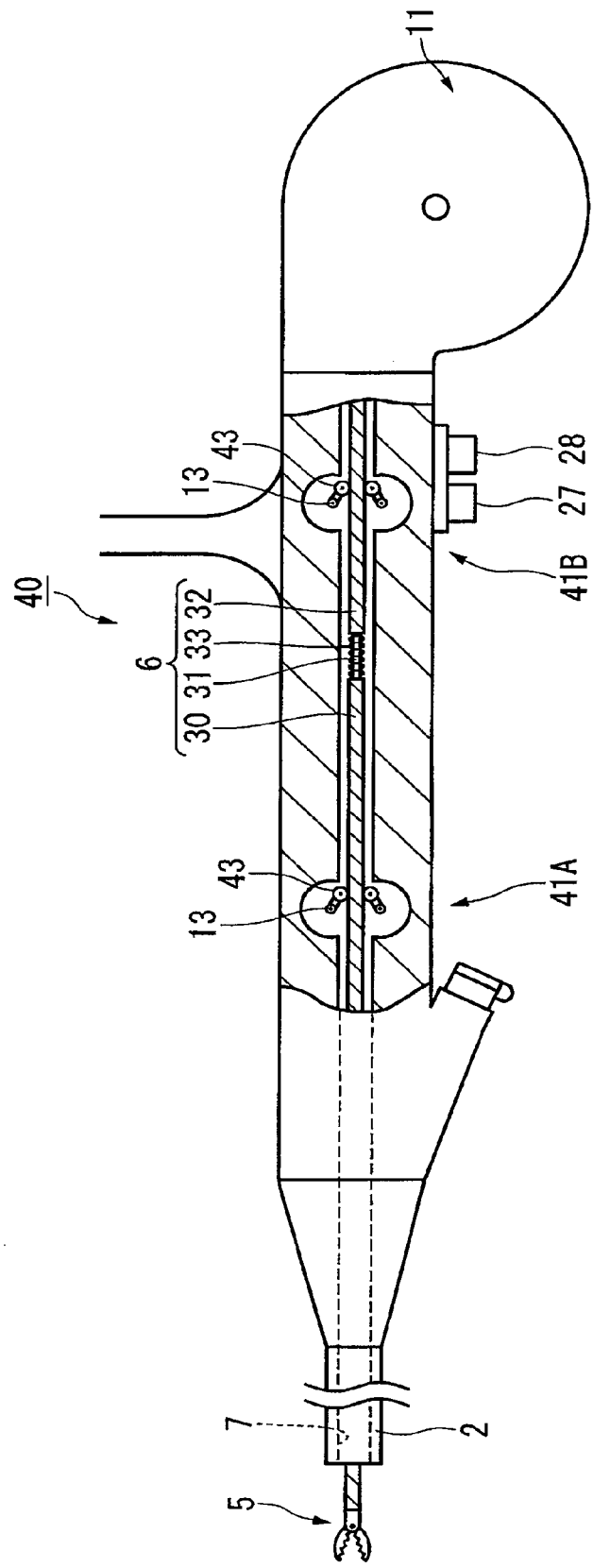
FIG. 12 is an explanatory view showing an operating method of the endoscope system according to the second embodiment of the present invention.

In this manner, in the same way as in the first embodiment, as is shown in FIG. 12, the forceps distal end portion 5 is opened.

In order for the forceps distal end portion 5 to grip tissue and then close, the operating switch 28 is operated so that the motor 12 of the second power transmission device 16B is rotated in a different direction from that described above.

Figure 13:
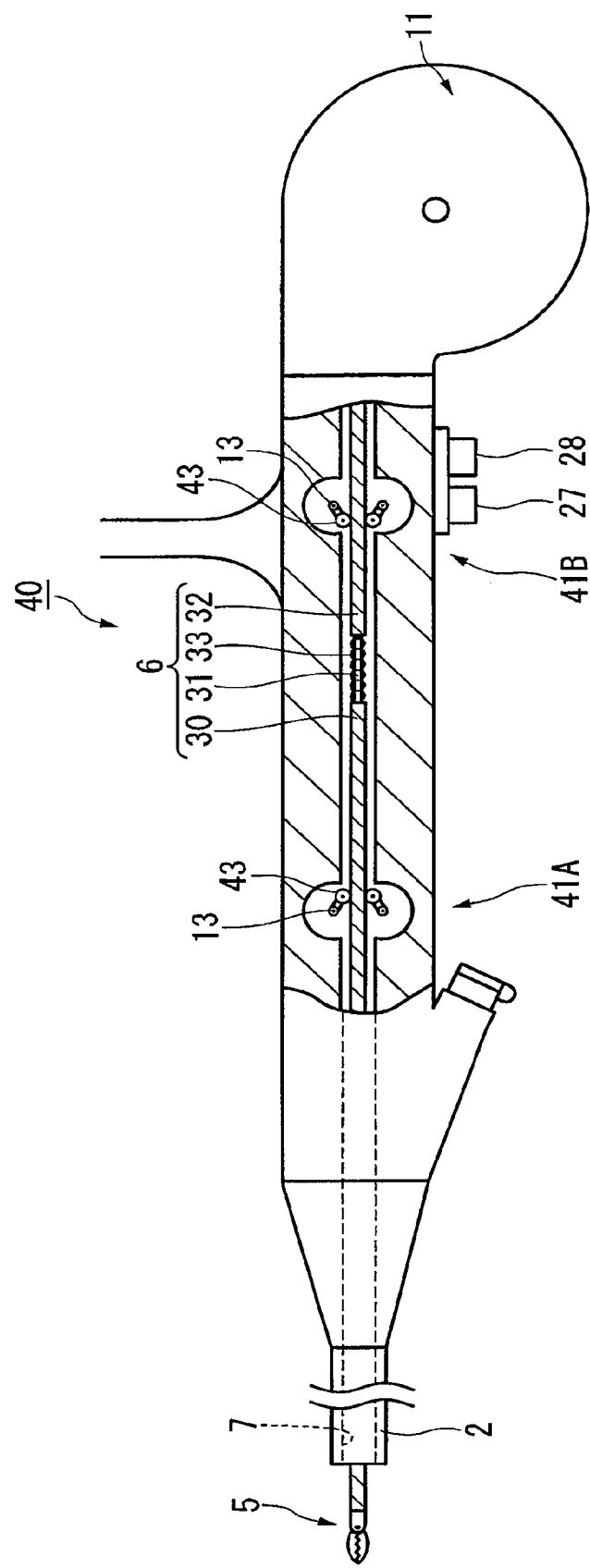
FIG. 13 is an explanatory view showing an operating method of the endoscope system according to the second embodiment of the present invention.

At this time, as the drive shafts 13 rotate, the supporting components 42 move away temporarily from the operating tube 32 taking the one end 42a as the center of rotation and move in this direction. As a result, they once again come into contact with the operating tube 32. After this contact, the rollers 43 rotate in a different direction from that described above while being pressed against the operating tube 32 so that, as is shown in FIG. 13, the operating tube 32 and the operating wire 31 are moved to the base end side of the channel 7, and the forceps distal end portion 5 is closed.

Figure 14:
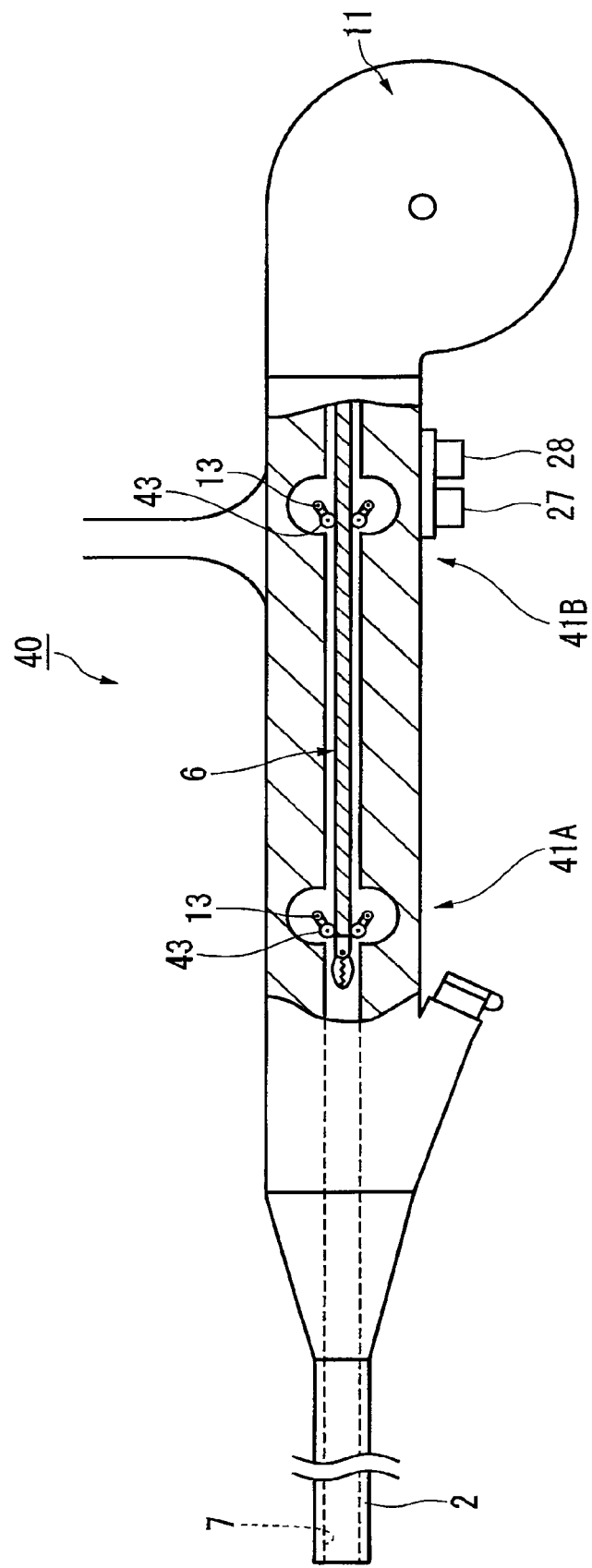
FIG. 14 is an explanatory view showing an operating method of the endoscope system according to the second embodiment of the present invention.

Next, the insertion/extraction switch 27 is operated thereby driving the respective motors 12 of the first power transmission device 16A and the second power transmission device 16B. At this time, the supporting components 42 and the rollers 43 of the first power transmission device 16A move away temporarily from the outer cannula 30 and revolve in this direction. As a result, they once again come into contact with the outer cannula 30. After this contact, the respective rollers 43 rotate while being pressed against the forceps insertion portion 6 so that, as is shown in FIG. 14, the forceps insertion portion 6 is moved to the base end side of the channel 7.

According to the endoscope system 40 of the present embodiment, when the drives shafts 13 are being rotated, it is possible to cause the supporting components 42 and the rollers 43 to rotate around the drive shafts 13 in the rotation direction of the drive shafts 13. Moreover, when the rollers 43 are in contact with the forceps insertion portion 6, the rotation of the drive shafts 13 is transmitted to the first pulley 44 thereby causing the endless belt 46 to rotate, and the rollers 43 can be made to rotate around the pivot center shafts 17 via the second pulleys 45. Accordingly, it is possible to obtain the same action and effects as those of the first embodiment.

Figure 15A:
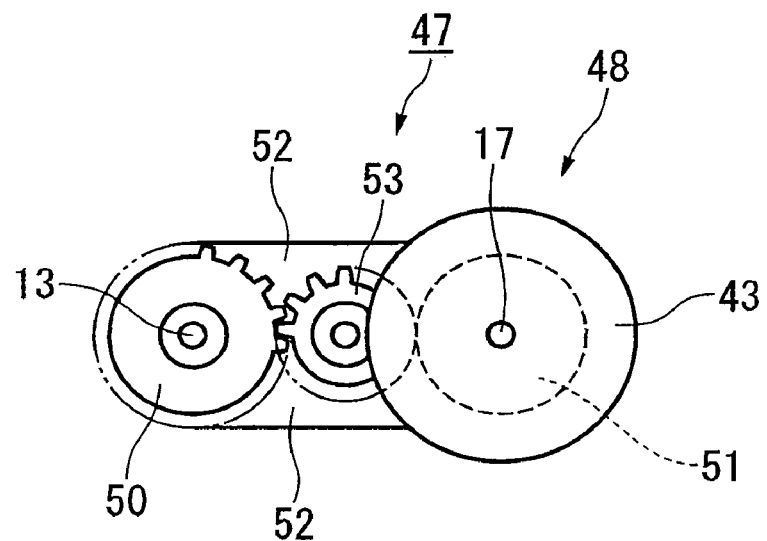
FIG. 15A is a plan view showing principal portions of a power transmission device of an endoscope system according to a third embodiment of the present invention.
Figure 15B:
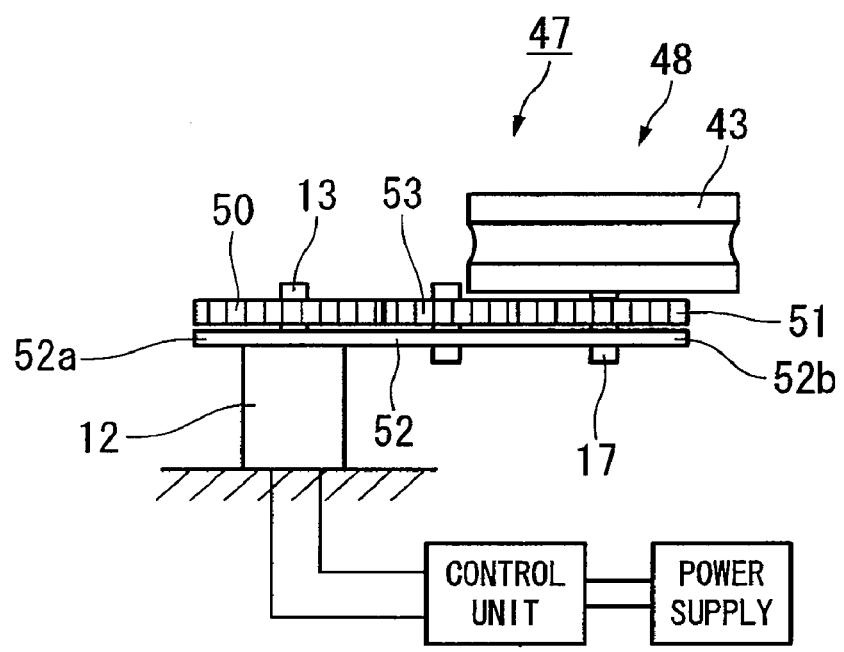
FIG. 15B is a side view showing principal portions of the power transmission device of the endoscope system according to the third embodiment of the present invention.
Figure 16:
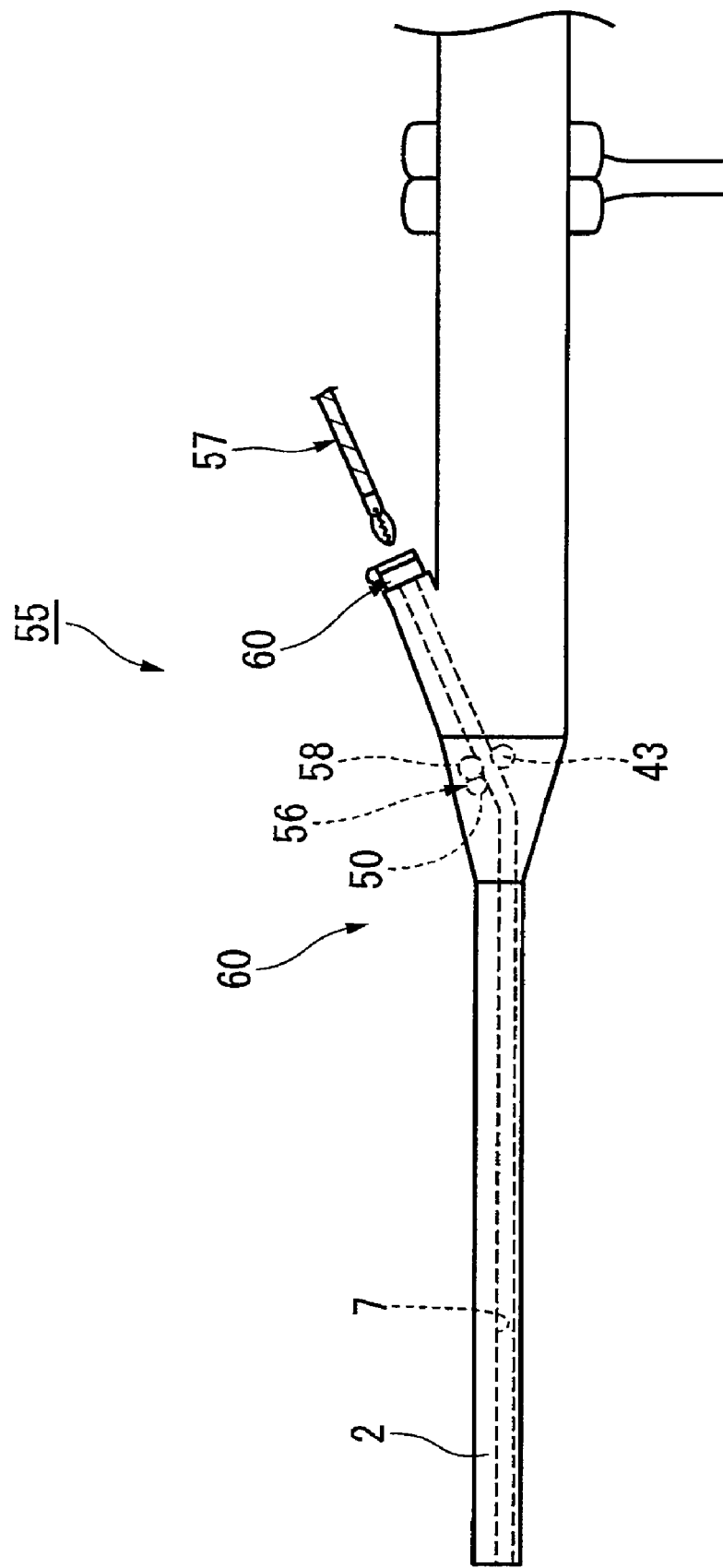
FIG. 16 is a side view including a partial cross-section which shows an endoscope system according to a fourth embodiment of the present invention.
Figure 17A:
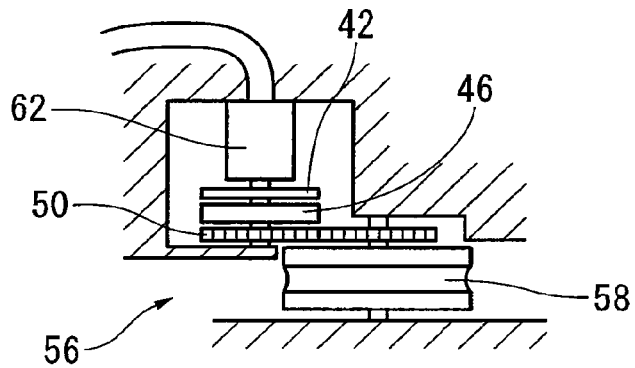
FIG. 17A is a front view showing principal portions of a power transmission device of the endoscope system according to the fourth embodiment of the present invention.
Figure 17B:
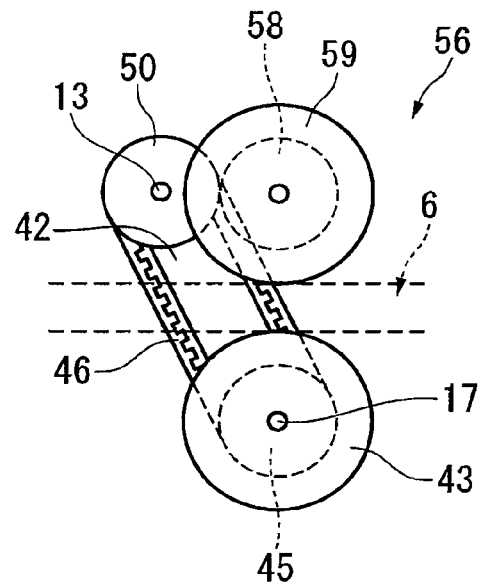
FIG. 17B is a side view showing principal portions of the power transmission device of the endoscope system according to the fourth embodiment of the present invention.
Figure 17C:
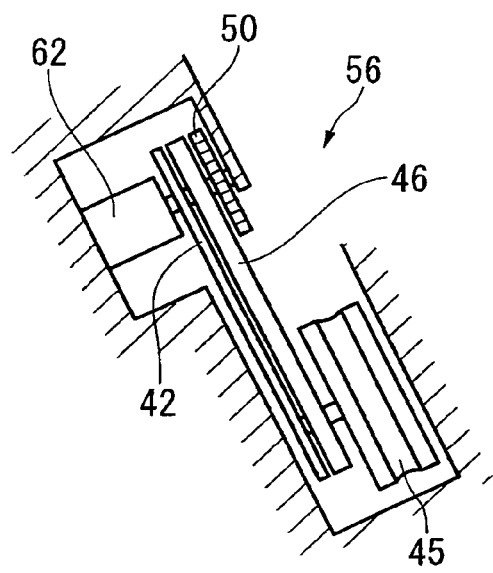
FIG. 17C is a rear view showing principal portions of the power transmission device of the endoscope system according to the fourth embodiment of the present invention.

Next, a third embodiment will be described with reference made to FIGS. 15A and 15B.

Note that component elements that are the same as those in the other embodiments described above are given the same descriptive symbols and a description thereof is omitted.

The third embodiment differs from the second embodiment in that a power transmission device 48 of an endoscope system 47 of the present embodiment is provided with a first gear 50 in place of the first pulley 44 that is connected to a drive shaft 13, a second gear 51 in place of the second pulley 45 that is connected to a roller 43, and a third gear 53 in place of the endless belt 46 that is able to pivot relative to a supporting component 52 and that meshes with the first gear 50 and the second gear 51.

The third gear 53 is pivotably supported between one end 52*a* and another end 52*b* of the supporting component 52.

Next, an operating method as well as actions and effects of the endoscope system 47 according to the present embodiment will be described.

Firstly, in the same way as in the second embodiment, the insertion portion 2 is inserted into a body cavity and the insertion/extraction switch 27 is operated. At this time, in conjunction with the rotation of the first gears 50 to which the drive shafts 13 are connected, the supporting components 52 rotate with the one end 52*a* as the center of rotation, while the rollers 43 revolve around the first gears 50 together with the second gears 51 and the third gears 53. In contrast, the rotation force of the first gears 50 is transmitted to the third gears 53, and is further transmitted to the second gears 51 so that the rollers 43 rotate in the same direction as the drive shafts 13.

The rollers 43 move in the rotation direction of the first gears 50 and approach the forceps insertion portion 6. After the rollers 43 have made contact with the forceps insertion portion 6, movement of the supporting components 53 is restricted so that the drive shafts 13 and supporting components 52 idle freely. Accordingly, the rollers 43 continue rotating together with the second gears 51. As a result, the forceps insertion portion 6 which is being pressed between the rollers 43 moves through the channel 7.

Subsequently, operations to insert and extract the forceps insertion portion 6 and also to open and close the forceps distal end portion 5 are performed by means of the same actions and consequent effects as those in the second embodiment.

According to this endoscope system 47, when the drive shafts 13 are rotated, it is possible to cause the supporting components 52, the rollers 43, and the third gears 53 to all revolve around the drive shafts 13 in the rotation direction of the drive shafts 13 using the same type of operating method as that of the second embodiment. Moreover, when the rollers 43 are in contact with the forceps insertion portion 6, the rotation of the drive shafts 13 is transmitted from the first gears 50 to the third gears 53 and causes the third gears 53 to revolve. It is then further transmitted to the second gears 51 and can cause the rollers 43 to rotate around the pivot center shafts 17.

Next, a fourth embodiment will be described with reference made to FIGS. 16, 17A, 17B, and 17C.

Note that component elements that are the same as those in the other embodiments described above are given the same descriptive symbols and a description thereof is omitted.

The fourth embodiment differs from the second embodiment in that a power transmission device 56 of an endoscope system 55 of the present embodiment is provided with a first gear 50 that is connected to a drive shaft 13, and a supporting roller 59 that is positioned facing the roller 43 via a forceps insertion portion 57 and has a gear 58 that meshes with the first gear 50.

The operating device 10 is not provided in this endoscope system 55. Instead of this, after the forceps insertion portion 57 has been inserted through a forceps aperture 61 of an endoscope 60, the forceps distal end portion 5 is manipulated by operating a forceps operating portion (not shown) that is connected to a base end of the forceps insertion portion 57. Note that a motor 62 is a brakeless type of motor, and when the motor 62 is not being driven, the drive shaft 13 is able to rotate freely.

Next, an operating method as well as actions and effects of the endoscope system 55 according to the present embodiment will be described.

Firstly, the forceps insertion portion 57 is inserted through the forceps aperture 61 into the channel 7, and the insertion/extraction switch 27 is operated so as to rotate the motor 62. At this time, the supporting roller 59 is made to rotate in a different direction from that of the drive shaft 13 by the rotation of the first gear 50 to which the drive shaft 13 is connected. In contrast, in conjunction with the rotation of the first pulley 44 to which the drive shaft 13 is connected, the supporting component 52 rotates with the one end 52*a* as the center of rotation, while the roller 43 revolves around the first pulley 44 in the rotation direction thereof together with the second pulley 45 that is connected to the other end 52*b*.

The roller 43 moves in the rotation direction of the first pulley 44 so as to approach the forceps insertion portion 57 and come into contact with the forceps insertion portion 57. At this time, as movement of the supporting component 57 is restricted, the drive shaft 13 and the supporting component 57 idle freely, and the rotation of the first pulley 44 is transmitted via the endless belt 46 to the second pulley 45 so that the roller 43 continues to rotate in the same direction as the drive shaft 13. As a result, the forceps insertion portion 57 which is being pressed between the roller 43 and the supporting roller 59 moves through the channel 7.

After the forceps distal end portion 5 has been made to protrude from the distal end of the channel 7, the insertion/extraction switch 27 is operated so that the motor 62 is stopped. In addition, the forceps distal end portion 5 is opened and closed by means of a forceps operating unit (not shown).

When removing the forceps insertion portion 57 from the channel 7, the forceps insertion portion 57 is extracted from inside the channel 7 and removed.

According to this endoscope system 55, it is possible to cause the supporting roller 59 to rotate via the first gear 50, and cause the roller 43 to revolve around the drive shaft so as to come into contact with the forceps insertion portion 57, and thereby press the forceps insertion portion 57 between the roller 43 and the supporting roller 59. Moreover, after this pressing, the roller 43 can be rotated in the opposite direction from the supporting roller 59 so that the forceps insertion portion 57 can be moved forwards or backwards inside the channel 7 while being pressed between the supporting roller 59 and the roller 43. Accordingly, when the forceps insertion portion 57 is being inserted or extracted through the forceps aperture 61, then this insertion or extraction can be performed irrespectively of any change in the diameter of the forceps insertion portion 57 by means of a single motor 62 and without requiring a complicated structure.

Figure 18:
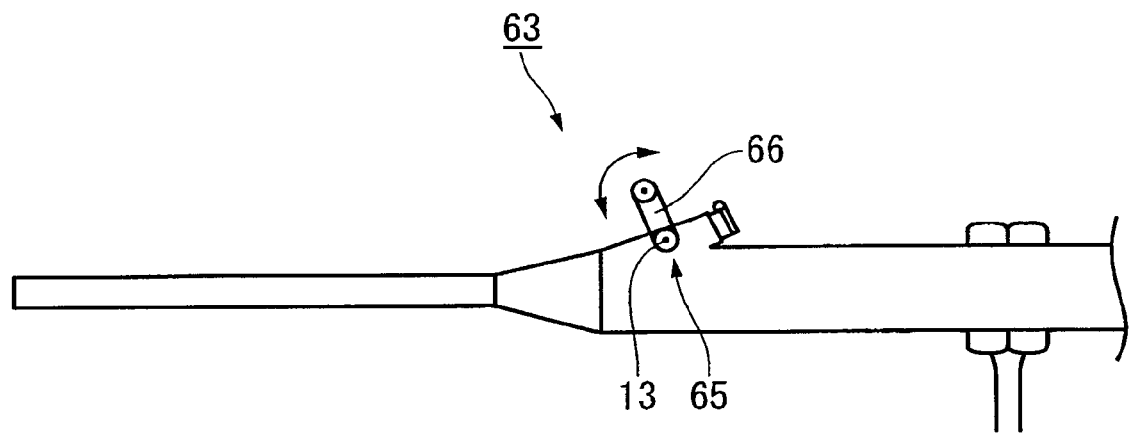
FIG. 18 is a side view including a partial cross-section which shows an endoscope system according to a fifth embodiment of the present invention.
Figure 19:
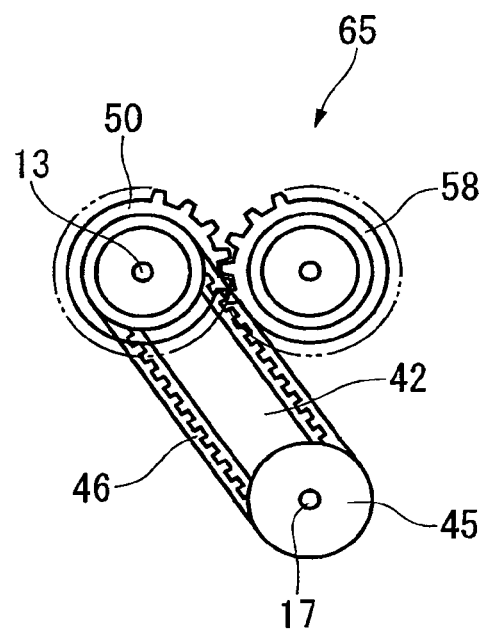
FIG. 19 is a plan view showing principal portions of a power transmission device of the endoscope system according to the fifth embodiment of the present invention.

Next, a fit embodiment will be described with reference made to FIGS. 18 and 19.

Note that component elements that are the same as those in the other embodiments described above are given the same descriptive symbols and a description thereof is omitted.

The fifth embodiment differs from the fourth embodiment in that, instead of the motor 62, a gripping portion 66 that is capable of rotating a drive shaft 13 is connected to a power transmission device 65 of an endoscope system 63 of the present embodiment.

According to this endoscope system 63, instead of driving the motor 62, it is possible to rotate the drive shaft 13 by rotating the gripping portion 66, and thereby obtain the same action and effects as those of the above described fourth embodiment.

Figure 20:
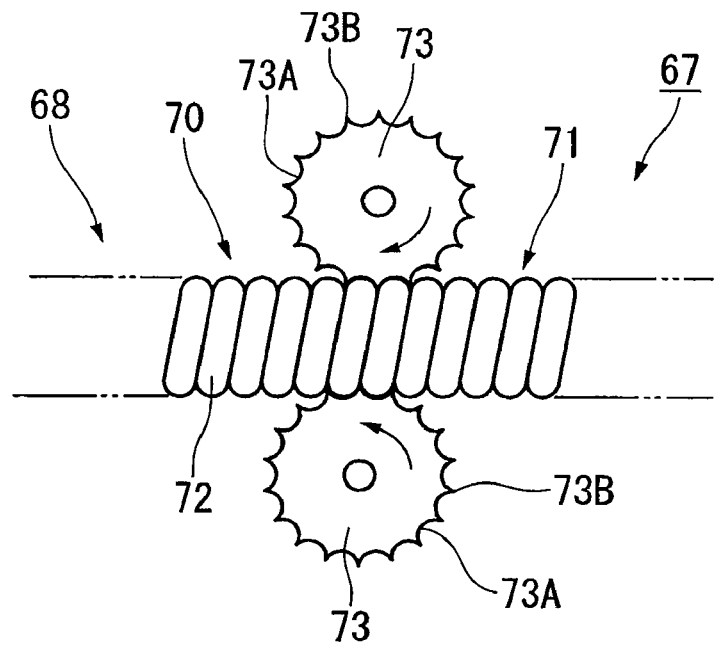
FIG. 20 is a side view showing principal portions of a power transmission device of an endoscope system according to a sixth embodiment of the present invention.

Next, a sixth embodiment will be described with reference made to FIG. 20.

Note that component elements that are the same as those in the other embodiments described above are given the same descriptive symbols and a description thereof is omitted.

The sixth embodiment differs from the first embodiment in that an outer cannula 70 and operating tube 71 of a forceps insertion portion 68 of an endoscope system 67 according to the present embodiment are formed by winding at least one wire 72 in a coil shape, and recessed portions 73A that are capable of meshing with the wire 72 and protruding portions 73B that are capable of meshing with gaps between adjacent wires 72 are formed alternatingly in a circumferential direction on an outer circumferential surface of the roller 73.

According to this endoscope system 67, as a result of the recessed portions 73A and protruding portions 73B meshing respectively, it is possible to increase the contact surface area between the outer circumferential surface of the roller 73 and the outer circumferences of the outer cannula 70 and operating tube 71, and rotation driving force from the roller 73 can be more effectively transmitted as forwards or backwards driving force for the outer cannula 70 and the operating tube 71.

Figure 21:
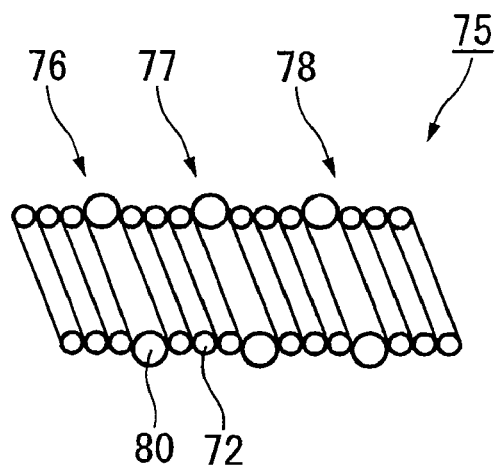
FIG. 21 is a side view showing principal portions of a power transmission device of an endoscope system according to a seventh embodiment of the present invention.

Next, a seventh embodiment will be described with reference made to FIG. 21.

Note that component elements that are the same as those in the other embodiments described above are given the same descriptive symbols and a description thereof is omitted.

The seventh embodiment differs from the sixth embodiment in that an outer cannula 77 and operating tube 78 of a forceps insertion portion 76 of an endoscope system 75 according to the present embodiment are formed by two types of wires 72 and 80, and the wire 80 is formed having a larger diameter than the wire 72.

According to this endoscope system 75, as a result of the contact between the large-diameter wire 80 and the roller 73, it is possible to increase the contact surface area between the outer circumferential surface of the roller 73 and the outer circumferences of the outer cannula 77 and operating tube 78, and rotation driving force can be more effectively transmitted as forwards or backwards driving force for the outer cannula 77 and the operating tube 78.

Figure 22:
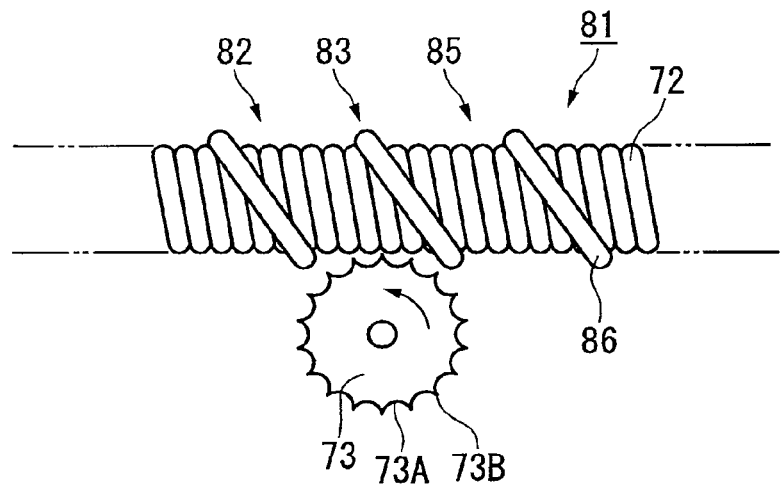
FIG. 22 is a side view showing principal portions of a power transmission device of an endoscope system according to an eighth embodiment of the present invention.

Next, an eighth embodiment will be described with reference made to FIG. 22.

Note that component elements that are the same as those in the other embodiments described above are given the same descriptive symbols and a description thereof is omitted.

The eighth embodiment differs from the sixth embodiment in that a wire component 86 is wound in a coil shape onto an outer circumference of an outer cannula 83 and operating tube 85 of a forceps insertion portion 82 of an endoscope system 81 according to the present embodiment.

According to this endoscope system 81, as a result of the contact between the wire component 86 and the roller 73, it is possible to increase the contact surface area between the outer circumferential surface of the roller 73 and the outer circumferences of the outer cannula 83 and operating tube 85, and rotation driving force can be more effectively transmitted as forwards or backwards driving force for the outer cannula.

Note that the technological range of the present invention is not limited to the above described embodiments and various modifications and the like may be made thereto insofar as they do not depart from the spirit or scope of the present invention.

Figure 23:
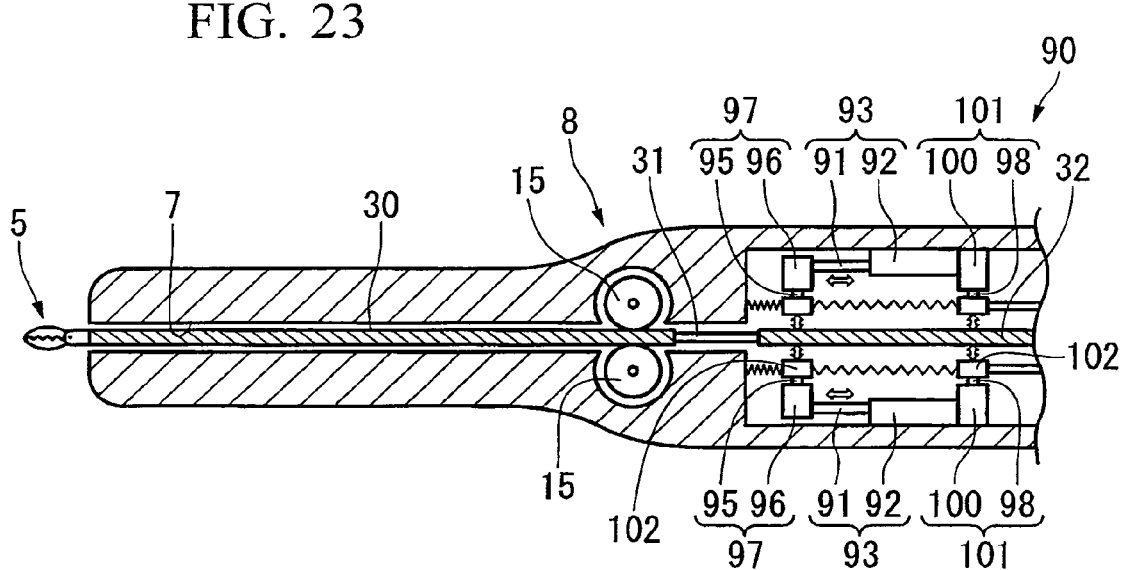
FIG. 23 is a side view including a partial cross-section which shows an endoscope system according to another embodiment of the present invention.

For example, in the above described embodiments, the operating device 10 has the same structure as the insertion/extraction device 8, however, as is shown in FIG. 23, it is also possible for an operating device 90 to be provided with forwards or backwards movement mechanisms 93 that have a first solenoid 92 that moves a first axial component 91 forwards or backwards in the axial direction of the channel 7, holding mechanisms 97 that are connected to a distal end side of the first axial components 91 and that have a second solenoid 96 that moves a second axial component 95 forwards or backwards in the radial direction of the channel 7, and restricting mechanisms 101 that are connected to a base end side of the first solenoids 92 and that have a third solenoid 100 that moves a third axial component 98 forwards or backwards in the radial direction of the channel 7.

In this case, protruding components 102 that can easily grip the forceps insertion portion 6 are positioned at distal ends of the second axial components 95 and the third axial components 98, and when the forceps insertion portion 6 is being inserted or extracted through the channel 7, it can be inserted or extracted quickly using the rapid rotation of the motor 12. Moreover, when the forceps distal end portion 5 is being manipulated, it is possible to perform the opening and closing operations using a mechanism having improved gripping force thanks to the higher torque obtained by using a solenoid.

Figure 24:
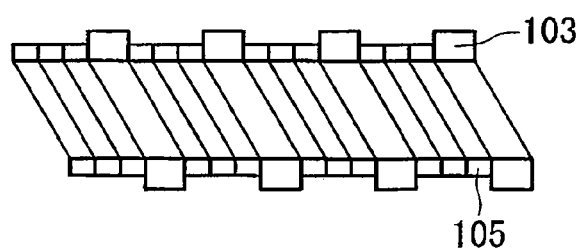
FIG. 24 is a side view showing principal portions of a power transmission device of the endoscope system according to the other embodiment of the present invention.

Moreover, the cross-section of the wires is not limited to being a circular cross-section as in the case of the wires 72 and 80, and as is shown in FIG. 24, wires 103 and 105 having a quadrangular cross-section may also be used.

In this case, workability can be further improved.

In this endoscope system, if drive shafts are rotated in a direction in which a treatment tool insertion portion that has been inserted into a channel is made to move forwards or backwards, rollers can be made to revolve around the drive shaft by means of a power transmission device, and the rollers and the treatment tool insertion portion can be brought into contact with each other. At this time, because the rollers can be made to rotate at positions where they are in contact with the treatment tool insertion portion even if treatment tool insertions portions having different outer diameters are being used, then irrespectively of the size of the outer diameter of the treatment tool insertion portion that is being inserted into or extracted from the channel, the rollers can be brought into contact with the treatment tool insertion portion. Moreover, after the rollers have been brought into contact with the treatment tool insertion portion, then the rollers can be rotated around their pivot center shafts in the same direction as the drive shafts while they are being pressed against the treatment tool insertion portion.

Moreover, the endoscope system according to the present invention is provided with a treatment tool distal end portion that is positioned at a distal end of the treatment tool insertion portion, and performs treatment after receiving forwards or backwards driving force, and an operating device that supplies the forwards or backwards driving force to the treatment tool distal end portion, and the operating device is provided with the drive shafts, the rollers, and the power transmission devices.

This endoscope system makes it possible to supply forwards or backwards driving force to a treatment tool distal end portion using the same method as is used to insert or extract a treatment tool insertion portion.

Moreover, in the endoscope system according to the present invention, the power transmission devices are formed as planetary gear mechanisms that are provided with a plurality of planetary gears and a sun gear, and the drive shafts are connected to one of the plurality of planetary gears, and the rollers are formed as internal gears that mesh with the planetary gears which are provided such that they are able to pivot around the sun gear.

In this endoscope system, when the drive shafts are rotated, the rollers which are internal gears and the sun gears can be made to revolve respectively around the planetary gears while they are being rotated. Moreover, when the rollers come into contact with the treatment tool insertion portion so that their revolving is prevented, the rollers rotate in those positions, thereby causing the treatment tool insertion portion to move in the rotation direction of the rollers.

Moreover, in the endoscope system of the present invention, the power transmission devices are provided with a supporting component that has one end that is slidably connected to the drive shaft and has another end that is supported such that it is able to pivot around the pivot center shaft of the roller, a first pulley that is connected to the drive shaft, a second pulley that is connected to the roller, and an endless belt that is wound around the first pulley and the second pulley.

In this endoscope system, when the drive shaft is rotated, the supporting component and the roller can be rotated around the drive shaft in the rotation direction of the drive shaft. Moreover, when the roller is in contact with the treatment tool insertion portion, the rotation of the drive shaft is transmitted to the first pulley and causes the endless belt to rotate. As a result, the roller can be made to rotate around its pivot center axis via the second pulley.

Moreover, in the endoscope system of the present invention, the power transmission devices are provided with a supporting component that has one end that is slidably connected to the drive shaft and has another end that is connected such that it is able to pivot around the pivot center shaft of the roller, a first gear that is connected to the drive shaft, a second gear that is connected to the roller, and a third gear that is provided such that it is able to pivot for the supporting component and meshes with the first gear and the second gear.

In this endoscope system, when the drive shaft is rotated, the supporting component, the roller, and the third gear can all be made to revolve around the drive shaft in the rotation direction of the drive shaft. Moreover, when the roller is in contact with the treatment tool insertion portion, the rotation of the drive shaft is transmitted from the first gear to the third gear and causes the third gear to rotate. It is then further transmitted to the second gear and causes the roller to rotate around its pivot center shaft.

The endoscope system according to the present invention is also an endoscope system in which the power transmission device is provided with a first gear that is connected to the drive shaft, and a supporting roller that faces the roller via the treatment tool insertion portion and meshes with the first gear.

In this endoscope system, by rotating the drive shaft, the supporting roller can be made to rotate via the first gear. In addition, the roller can be made to revolve around the drive shaft so as to come into contact with a treatment tool insertion portion and the treatment tool insertion portion can be pressed between the roller and the supporting roller. Moreover, after being pressed, the roller can be made to rotate in the opposite direction from the supporting roller so that the treatment tool insertion portion can be moved forwards or backwards inside the channel.

The endoscope system according to the present invention is also an endoscope system in which a gripping portion that is able to rotate the drive shaft is connected.

In this endoscope system, by gripping the gripping portion and rotating it around the drive shaft, it is possible to manually rotate the drive shaft.

Moreover, the endoscope system according to the present invention is an endoscope system in which the treatment tool insertion portion is provided with an outer cannula that is formed by winding at least one wire in a coil shape, and recessed portions that are capable of meshing with the wire and protruding portions that are capable of meshing with gaps between adjacent wires are formed alternatingly in a circumferential direction on an outer circumferential surface of the roller.

According to this endoscope system, as a result of the recessed portions and protruding portions meshing respectively, it is possible to increase the contact surface area between the outer circumferential surface of the roller and the outer circumferences of the outer cannula, and rotation driving force can be more effectively transmitted as forwards or backwards driving force for the outer cannula.

Moreover, the endoscope system according to the present invention is an endoscope system in which a plurality of the aforementioned wires are provided, and at least one of the wires is formed having a larger diameter than the other wires.

In this endoscope system, as a result of the contact between the wire portion which has the larger diameter and the roller, it is possible to increase the contact surface area between the outer circumferential surface of the roller and the outer circumference of the outer cannula, and rotation driving force can be more effectively transmitted as forwards or backwards driving force for the outer cannula.

Moreover, the endoscope system according to the present invention is an endoscope system in which a wire component is wound in a coil shape onto an outer circumference of the outer cannula.

In this endoscope system, as a result of the contact between the wire component and the roller, it is possible to increase the contact surface area between the outer circumferential surface of the roller and the outer circumference of the outer cannula, and rotation driving force can be more effectively transmitted as forwards or backwards driving force for the outer cannula.

According to the present invention, it is possible to press rollers against a treatment tool insertion portion using a single rotation drive source and thereby insert or extract the treatment tool insertion portion even if treatment tool insertion portions having different outer diameters are being used.

INDUSTRIAL APPLICABILITY

As a practical example of the present invention, the present invention can be favorably applied to an endoscope system in which, by means of a single rotation driving source rollers can be pressed against treatment tool insertion portions having different outer diameters, and the treatment tool insertion portion can be inserted or extracted.

What is claimed is:
1. An endoscope system comprising:
a flexible treatment tool insertion portion;
an operating unit;
a channel through which the treatment tool insertion portion can be inserted; and
an insertion/extraction device configured to insert the treatment tool insertion portion into the channel and extract the treatment tool insertion portion from within the channel,
a treatment tool distal end portion that is positioned at a distal end of the treatment tool insertion portion, and configured to perform treatment after receiving forwards or backwards driving force,
an operating device configured to supply the forwards or backwards driving force to the treatment tool distal end portion, wherein
the insertion/extraction and the operating device are provided with:
drive shafts that are driven by a pivot drive source to pivot;
rollers that have rotation center shafts, and that are configured to receive pivot driving force from the drive shafts, and are thereby able to pivot around the rotation center shafts; and
a first power transmitting device that is positioned adjacent a distal end side of the operating unit, and configured to transmit pivot driving force from the drive shafts to the rollers,
a second power transmitting device that is positioned adjacent a proximal end side of the operating unit, and configured to transmit pivot driving force from the drive shafts to the rollers,
a position of the rotation center shafts being such that, in case of the rollers contact with the treatment tool insertion portion, it is different from a position of the rotation center shafts, in case of the rollers not being in contact with the treatment tool insertion portion,
the rotation center shafts being configured such that they can be made to revolve around the drive shafts by rotation driving force from the drive shafts,
a revolution radius being defined by a distance between the rotation center shafts and the drive shafts, with a first distance, which is obtained by adding a radius of the rollers to the revolution radius, is a longer distance than a second distance between the drive shafts and the treatment tool insertion portion,
the first and second power transmitting devices being configured to cause the rotation center shafts to revolve around the drive shafts, and to cause the rollers to rotate around the pivot center shafts,
the insertion/extraction device being configured to operate the first and second power transmitting devices so as to move the treatment tool insertion portion forwards or backwards, and
the operating device being configured to operate the second power transmitting device so as to perform treatment with the treatment tool distal end portion.

2. The endoscope system according to claim 1, wherein the first and second power transmission devices are formed as planetary gear mechanisms that are provided with a plurality of planetary gears and a sun gear, the drive shafts are connected to one of the plurality of planetary gears, and the rollers are formed as internal gears that mesh with the planetary gears which are provided such that they are able to pivot around the sun gear.

3. The endoscope system according to claim 1, wherein the power transmission devices are provided with
a supporting component that has one end that is slidably connected to the drive shaft and has another end that is supported such that it is able to pivot around the pivot center shaft of the roller,
a first pulley that is connected to the drive shaft, a second pulley that is connected to the roller, and
an endless belt that is wound around the first pulley and the second pulley.

4. The endoscope system according to claim 1, wherein the power transmission devices are provided with
a supporting component that has one end that is slidably connected to the drive shaft and has another end that is pivotably connected to the pivot center shaft of the roller,
a first gear that is connected to the drive shaft, a second gear that is connected to the roller, and
a third gear that is provided such that it is able to pivot for the supporting component and meshes with the first gear and the second gear.

5. The endoscope system according to claim 3 wherein the power transmission device is provided with:
a first gear that is connected to the drive shaft; and
a supporting roller that faces the roller via the treatment tool insertion portion and meshes with the first gear.

6. The endoscope system according to claim 1 wherein a gripping portion that is able to rotate the drive shaft is connected.

7. The endoscope system according to claim 1 further comprising:
the treatment tool insertion portion being provided with an outer cannula that is formed by winding at least one wire in a coil shape,
recessed portions formed on an outer circumferential surface of the rollers that are configured to be capable of meshing with the wire,
protruding portions formed on an outer circumferential surface of the rollers that are configured to be capable of meshing with gaps between the wire and adjacent the wire, wherein
the recessed and protruding portions are formed alternatingly in a circumferential direction.

8. The endoscope system according to claim 7 wherein a plurality of the wires are provided, and at least one of the wires is formed having a larger diameter than the other wires.

9. The endoscope system according to claim 7 wherein a wire component is wound in a coil shape onto an outer circumference of the outer cannula.

* * * * *